(12) United States Patent
Faber

(10) Patent No.: US 9,387,443 B2
(45) Date of Patent: *Jul. 12, 2016

(54) HYDROPHOBIC CELLULOSE MEMBRANE, METHOD FOR THE PRODUCTION THEREOF, AND USE OF SAME IN HYDROPHOBIC INTERACTION CHROMATOGRAPHY

(75) Inventor: René Faber, Göttingen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 615 days.

This patent is subject to a terminal disclaimer.

(21) Appl. No.: 12/937,857

(22) PCT Filed: Feb. 10, 2009

(86) PCT No.: PCT/EP2009/000914
§ 371 (c)(1),
(2), (4) Date: Feb. 3, 2011

(87) PCT Pub. No.: WO2009/127286
PCT Pub. Date: Oct. 22, 2009

(65) Prior Publication Data
US 2011/0120947 A1 May 26, 2011

(30) Foreign Application Priority Data

Apr. 14, 2008 (DE) .......................... 10 2008 018 734

(51) Int. Cl.
*B01D 71/10* (2006.01)
*B01D 67/00* (2006.01)
(Continued)

(52) U.S. Cl.
CPC .......... *B01D 67/0093* (2013.01); *B01D 15/327* (2013.01); *B01D 69/02* (2013.01);
(Continued)

(58) Field of Classification Search
None
See application file for complete search history.

(56) References Cited

U.S. PATENT DOCUMENTS 4,147,622 A * 4/1979 Nussbaumer ................ 210/651
5,739,316 A 4/1998 Beer et al.
(Continued)

FOREIGN PATENT DOCUMENTS

DE 4323913 A1 1/1995
DE 10 2004 053 787 A1 5/2006
(Continued)

OTHER PUBLICATIONS

International Search Report dated May 27, 2009, for International Application No. PCT/EP2009/000914.
(Continued)

*Primary Examiner* — Krishnan S Menon
(74) *Attorney, Agent, or Firm* — Knobbe, Martens, Olson & Bear, LLP

(57) ABSTRACT

There is provided a crosslinked cellulose hydrate membrane having a porous double structure which consists of micropores having a diameter in the range from >100 nm to 20 μm and ultrapores which have a diameter of <100 nm and which are not accessible to Blue Dextran having an average molecular weight Mw of 2 000 000, wherein the fraction of the volume of the ultrapores is more than 15% of the entire pore volume accessible to water, and wherein hydrophobic ligands, selected from $C_1$-$C_{20}$-alkyl and their derivatives or $C_6$-$C_{25}$-aryl and their derivatives or $C_7$-$C_{25}$-arylalkyl and their derivatives or —[$(CH_2)_m$—O—]$_n$—R, where m is 2 or 3, n is a whole number greater than or equal to 1, and R is —H or —$C_1$-$C_5$-alkyl, are bonded to the membrane. In addition, methods for producing the membrane, an apparatus for hydrophobic interaction chromatography and comprising the membrane, and the use of the membrane in hydrophobic interaction chromatography are specified.

19 Claims, 8 Drawing Sheets

Figure 1:
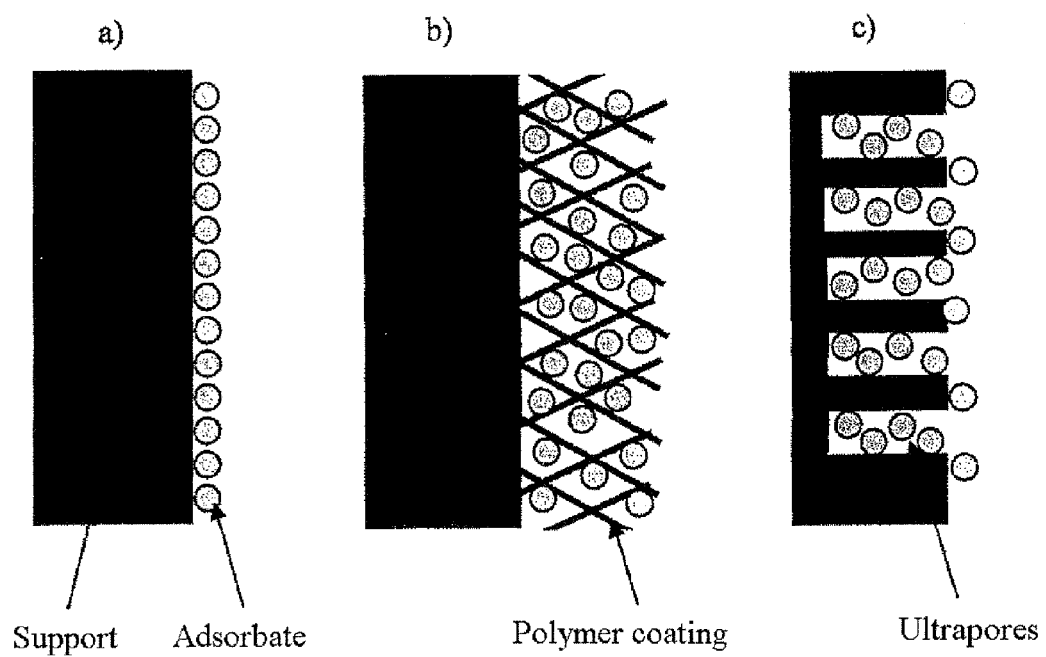

(51) Int. Cl.
*B01D 69/02* (2006.01)
*B01D 15/32* (2006.01)
*B01J 20/26* (2006.01)
*B01J 20/28* (2006.01)
*B01J 20/285* (2006.01)
*C07K 1/30* (2006.01)
*C08B 15/10* (2006.01)

(52) U.S. Cl.
CPC .............. *B01D 71/10* (2013.01); *B01J 20/262* (2013.01); *B01J 20/265* (2013.01); *B01J 20/267* (2013.01); *B01J 20/285* (2013.01); *B01J 20/28033* (2013.01); *B01J 20/28078* (2013.01); *C07K 1/30* (2013.01); *C08B 15/10* (2013.01); *B01D 2323/16* (2013.01); *B01D 2323/30* (2013.01); *B01D 2323/36* (2013.01); *B01D 2325/02* (2013.01); *B01D 2325/12* (2013.01); *B01D 2325/14* (2013.01); *B01D 2325/16* (2013.01)

(56) References Cited

U.S. PATENT DOCUMENTS

| | | | |
|---|---|---|---|
| 6,103,121 | A | 8/2000 | Bhattacharyya et al. |
| 2003/0038081 | A1* | 2/2003 | Wang et al. .................... 210/651 |
| 2004/0069707 | A1 | 4/2004 | Naldrett |
| 2007/0244307 | A1* | 10/2007 | Engstrand et al. ............. 530/417 |
| 2008/0179248 | A1* | 7/2008 | Axen et al. ..................... 210/650 |
| 2010/0059440 | A1 | 3/2010 | Rudstedt et al. |

FOREIGN PATENT DOCUMENTS

| | | |
|---|---|---|
| EP | 0586268 B1 | 2/2000 |
| WO | WO 03/015902 A2 | 2/2003 |
| WO | 2007017085 A2 | 2/2007 |
| WO | WO 2007/017085 A2 | 2/2007 |
| WO | WO 2008/095709 A1 | 8/2008 |

OTHER PUBLICATIONS

Hermanson, et al., "Immobilized Affinity Ligand Techniques", Academic Press, Inc., San Diego, 1992, in 104 pages. (Duo to the large file size, this document is divided and filed in three separate parts).

\* cited by examiner

Lysozyme bound to the adsorptively active polymer layer

Membrane-penetrating micropores

Coarse structure of relatively thick fibers of the cellulose or their agglomerates, adsorptively inactive More finely distributed fibroid or clusterlike membrane material Membrane-penetrating micropores Coarse structure of relatively thick fibers of the cellulose or their agglomerates, with bound lysozyme More finely distributed fibroid or clusterlike membrane material, with bound lysozyme Membrane-penetrating micropores Coarse structure of relatively thick fibers of the cellulose or their agglomerates with ultrapores accessible to biomolecules, with bound lysozyme More finely distributed fibroid or clusterlike membrane material with ultrapores accessible to biomolecules, with bound lysozyme Figure 6: Protein separation according to example 15 with butyl membrane
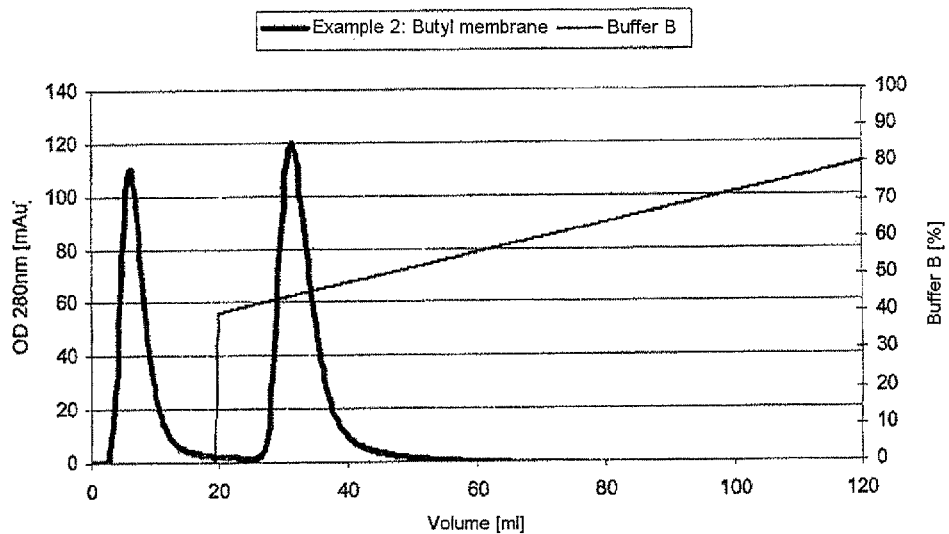
Figure 7: Protein separation according to example 15 with phenyl membrane
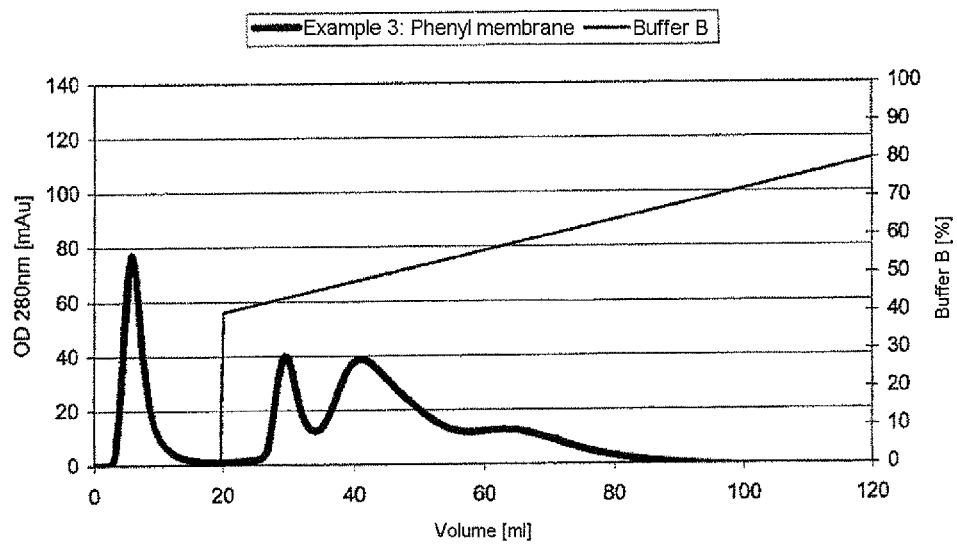

Figure 8: Protein separation according to example 15 with hexyl membrane
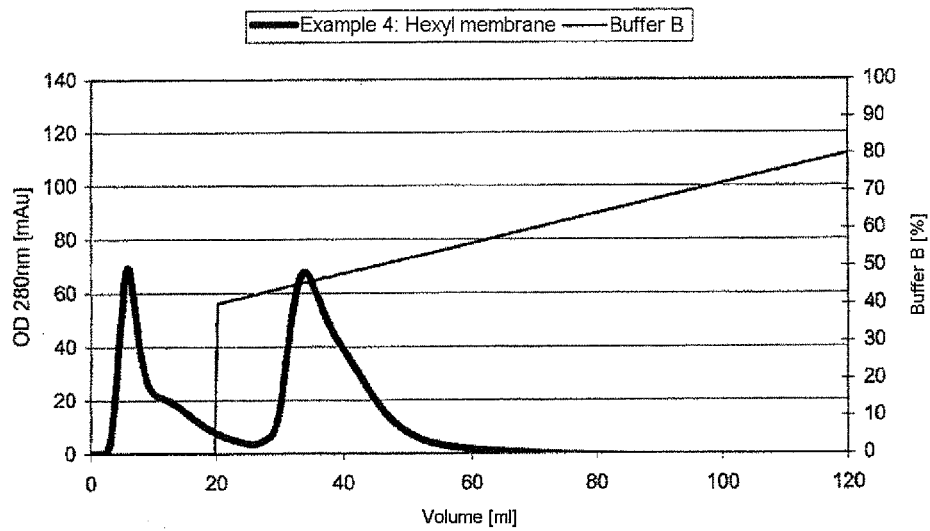
Figure 9: Protein separation according to example 15 with octyl membrane
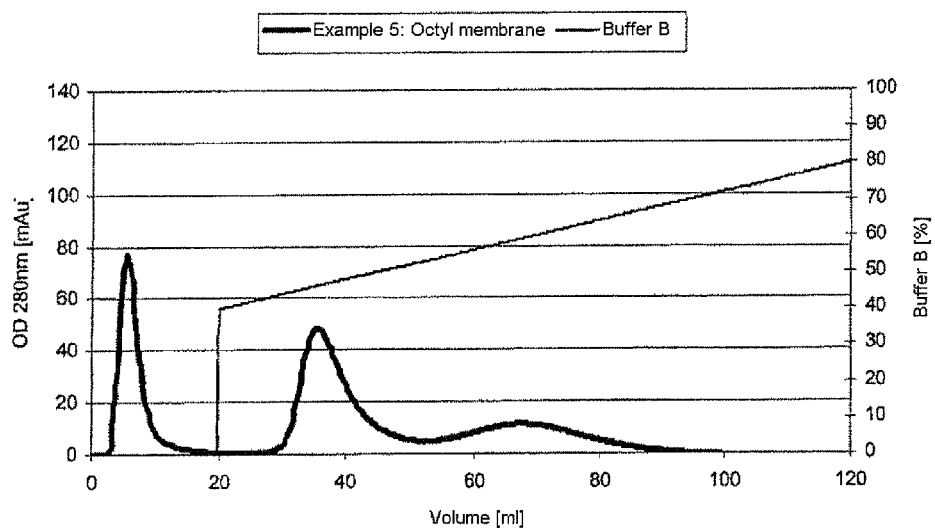

HYDROPHOBIC CELLULOSE MEMBRANE, METHOD FOR THE PRODUCTION THEREOF, AND USE OF SAME IN HYDROPHOBIC INTERACTION CHROMATOGRAPHY

This application is the U.S. National Phase of International Application No. PCT/EP2009/000914, filed Feb. 10, 2009, designating the U.S. and published in German as WO 2009/127286 on Oct. 22, 2009 which claims the benefit of German Patent Application No. 10 2008 018 734.8, filed Apr. 14, 2008.

The present invention relates to adsorbents for adsorptive material separation in liquid media by virtue of a hydrophobic interaction and also apparatuses which comprise the adsorbents according to the invention. More particularly, the present invention relates to a cellulose hydrate membrane, methods for its production, and also its use in hydrophobic interaction chromatography.

The following definitions and facts underlie the description of the invention, wherein "flow rate" is understood to mean hydraulic permeability.

Flat adsorbents with pores passing from one side to the other side are referred to as adsorption membranes. Adsorbents are porous solids which can selectively form bonds with certain components of fluids via functional surface groups referred to as ligands. Target substance(s) and/or contaminant(s) are, according to the invention, referred to as adsorbates, and they can also be various different substances. Adsorbates can be single molecules, associates, or particles which are, in each case, preferably proteins or other substances of biological origin.

With regard to ligands which interact with the adsorbate(s), mention can be made, by way of example, of ion exchangers, chelating agents and heavy metal chelates, thiophilic, hydrophobic ligands of various chain lengths and configurations, reversed-phase systems, dye ligands, affinity ligands, amino acids, coenzymes, cofactors and their analogs, substrates and their analogs, endocrine and exocrine substances, such as hormones and active ingredients acting like hormones, effectors and their analogs, enzyme substrates, enzyme inhibitors and their analogs, fatty acids, fatty acid derivatives, conjugated fatty acids and their analogs, nucleic acids, such as DNA, RNA, and their analogs and derivatives (single-, double-, and/or multistranded), and also peptide nucleic acids and their derivatives, viruses, virus particles, monomers and their analogs and derivatives, oligomers to polymers and their analogs and derivatives, high-molecular-weight carbohydrates, which can be linear or branched, unsubstituted or substituted, polymeric glycoconjugates, such as heparin, amylose, cellulose, chitin, chitosan, and their monomers and oligomers and derivatives and analogs thereof, lignin and its derivatives and analogs, other biochemical ligands, such as oligopeptides and polypeptides, e.g., proteins and their oligomers, multimers, subunits and also parts thereof, more particularly lectins, antibodies, fusion proteins, haptens, enzymes, and subunits and also parts thereof, structural proteins, receptors and effectors and also parts thereof, and in addition xenobiotics, pharmaceuticals and pharmaceutical active ingredients, alkaloids, antibiotics, biomimetics, etc.

An adsorbent can, at the same, also carry two or more types of functional groups on its inner and outer surface.

The binding of the adsorbates to the adsorbent can be reversible or irreversible; in any case, it makes possible their separation from the fluids, which are generally aqueous liquids and referred to hereinafter as media. The term "elution" summarizes the desorption and the accompanying rinse steps, etc., and the liquid used for elution is the "eluent". The components can represent one or more target substances and/or one or more contaminants. "Target substances" are valuable materials which are to be recovered in an enriched or pure form from the medium. "Contaminants" are materials whose absence is required or desirable for technical, regulatory, or other reasons. For the removal of contaminants, which is referred to as "negative adsorption", the adsorption can (may) proceed irreversibly when the adsorbent is to be used only once. In the case of adsorption of target substance(s), the process must proceed reversibly. Either a mere enrichment or a separation into multiple target substances can be carried out, in which latter case either the adsorption, the desorption, or both can take place selectively.

The process is referred to as adsorptive material separation or chromatography. Conventional adsorbents for chromatography are in particulate form and are used in the form of packings in columns. In contrast to this, adsorption membranes are generally employed in modules whose designs correspond to the modules which are usually customary in membrane filtration (e.g., spiral-wound module, stack module, etc.). The requirements for mechanical strength are comparable with those to be applied to filtration membranes and are thus substantially higher than for particulate adsorbents, for which fragile support materials, such as gels of dextran or agarose, have established themselves so universally that the term "gels" has become established as a synonym for them. In contrast, there is the same basic requirement for all membranes and gels, this being very low nonspecific adsorption.

The implementation of chromatographic separation with the help of adsorption membranes is also referred to as membrane chromatography, and all of the synthetic and natural ligands known in chromatography can also be used in the same way for adsorption membranes. The bonding of the ligand to the support can be preceded by an "activation" of the support, i.e., the introduction of reactive, functional groups which are capable of spontaneous bonding of the ligand. In rarer cases, the ligand itself has a reactive group, such as, for example, the reactive dyes, serving as dye ligands, from the textile industry. Techniques for bonding functional groups are known per se to a person skilled in the art (e.g., from Greg T. Hermanson, A. Krishna Mallia, Paul K. Smith, Immobilized Affinity Ligand Techniques, Academic Press, INC, 1992).

The amount of adsorbate, based on the amount of the adsorbent, which becomes bound per loading in equilibrium with the medium, i.e., the specific binding capacity of the adsorbent, is, for a given ligand density, proportional to its specific surface area. The specific surface area of porous structures increases with decreasing pore size; as a result, its specific binding capacity also increases, provided that the exclusion limit of the pores, i.e., that molar mass above which entry of a molecule is not possible, does not fall below the molar mass of the adsorbate.

Separation materials for reversed-phase chromatography (RPC) and hydrophobic interaction chromatography (HIC) and their production are known, for example, from DE 43 23 913 A1. They are separation materials for hydrophobic chromatography on the basis of hydroxyl-group-containing base supports on whose surfaces polymers are covalently bonded.

In the prior art, customary supports are uncrosslinked or crosslinked polysaccharides, such as, for example, Sepharose gels from GE Healthcare, and also crosslinked poly(meth)acrylates in the form of porous, spherical gels. These are mostly substituted with alkyl or aryl residues, e.g., butyl, hexyl, or phenyl residues. A customary method for producing these adsorbents is based on reacting a support, which is activated with oxirane groups, with an alcohol in the presence of boron trifluoride etherate. Other production methods are based on reacting a hydroxyl-group-containing support with an oxirane-group-containing molecule in the presence of boron trifluoride etherate. Other methods for producing hydrophobic adsorbents are based on reacting oxirane-containing activated supports with amines.

Two groups of ligands, which are applied to supports, are customary for adsorptive material separation by virtue of a hydrophobic interaction:

Ligands for reversed-phase chromatography, which lead to high hydrophobicity of the matrix, are used mainly for separating small adsorbates. Customary ligands consist of $C_8$- or $C_{18}$-alkyl residues.

Ligands for hydrophobic interaction chromatography (HIC), which lead to lower hydrophobicity of the matrix, are used mainly for separating large adsorbates, such as proteins in aqueous media. Frequently used ligands are, for example, $C_4$-alkyl residues, $C_6$-alkyl residues, phenyl residues, or polymers, such as polyethylene glycol or polypropylene glycol.

When particulate adsorbents are used for producing an adsorbent, a number of disadvantages arises:
1. The loading of an adsorber with the appropriate adsorbent is laborious, since any irregularity, channel formation, and suchlike must be avoided. There are also unavoidable, disadvantageous boundary effects between the adsorbent and the housing of the adsorber.
2. There is antagonism between pressure drop and transport kinetics such that the latter is favored by decreasing particle sizes, which, however, increase the pressure drop at the same time.
3. Further disadvantages of liquid-chromatographic material separations with particulate adsorbents are in their slow mode of operation owing to the diffusion limitation of mass transfer.

The slow mode of operation of conventional chromatography columns can lead to long retention times of target molecules in the column and, resulting from this, to irreversible damage to the target molecules (e.g., through a change in the three-dimensional protein structure).

Membranes can also be used for hydrophobic interaction chromatography. The membranes known in the prior art for this purpose are based mainly on grafted hollow fiber membranes. With regard to this, see, for example, the articles by Kubota in Reactive & Functional Polymers 29 (1996) 115-122, "Control of phenyl-group site introduced on the graft chain for hydrophobic interaction chromatography", and by Kubota in Journal of Chromatography A, 718 (1995) 27-34, "Preparation of a hydrophobic porous membrane containing phenyl groups and its protein adsorption performance".

A 0.2 µm polyethylene (PE) hollow fiber membrane grafted with glycidyl methacrylate (GMA) by means of electron beams (inner diameter of 0.7 mm, outer diameter of 1.2 mm, wall thickness of 250 µm) was partially reacted with phenol, and remaining epoxide groups were hydrolyzed with sulfuric acid. The phenyl-modified membrane thus produced was tested for the binding of bovine serum albumin (BSA). The phenyl ligand density was 0.53-0.64 mol/kg at a 14-17% partial conversion with phenol. A solution of 0.2 mg/ml BSA in a 0.07 M phosphate buffer, pH 7.4, 2 M $(NH_4)_2SO_4$ was used for the adsorption. Washing was done with a 0.07 M phosphate buffer, pH 7.4, 2 M $(NH_4)_2SO_4$, and elution was done with a 0.07 M phosphate buffer, pH 7.4.

The binding capacity was 33-37 mg of BSA per g of adsorbent, with the recovery of the target substance in the eluate being up to 80%. The base membrane (grafted and completely hydrolyzed) showed about 50% of the binding capacity of the membrane reacted with phenol (degree of conversion of 15%).

The article by Kawai in Journal of Chromatography B, 790 (2003) 131-142, "Protein binding to polymer brush, based on ion-exchange, hydrophobic and affinity interactions", describes a polyethylene (PE) or polypropylene (PP) hollow fiber membrane which was grafted with glycidyl methacrylate (GMA) by means of electron beams and which was reacted with phenol and butanol. The binding capacity for BSA corresponds to the theoretically calculated monolayer binding. No swelling of the grafted layer occurred.

The article by Saito in Journal of Chromatography, 586 (1991) 27-33, "Protein adsorption capacity of a porous phenylalanine-containing membrane based on a polyethylene matrix", describes a PE hollow fiber membrane which was grafted with glycidyl methacrylate (GMA) by means of electron beams and which has phenylalanine groups bonded via epoxide groups (inner diameter of 0.62 mm, outer diameter of 1.24 mm, wall thickness of 310 µm).

Bovine gamma-globulin in 0.01 M Tris/HCl, pH 8.0, 3.3 M NaCl was used for the adsorption, and elution was carried out with 0.01 M Tris/HCl, pH 8.0, 1-2 M NaCl.

The binding capacity was 30 to 50 mg of bovine gamma-globulin per g of adsorbent, with the recovery of the target substance in the eluate being up to 80%.

In addition, it is known in the prior art that there are flat membranes which do not carry any functional groups, but which can be used for HIC in combination with filtration owing to their hydrophobic properties.

The article by Ghosh in Journal of Immunological Methods 314 (2006) 1-8, "Purification of humanized monoclonal antibodies by membrane-based hybrid bioseparation technique", describes an unmodified polyvinylidene fluoride (PVDF) membrane from Millipore having a pore diameter of 0.22 µm for a combination of filtration and hydrophobic interaction chromatography for antibody purification.

Furthermore, it is known in the prior art that there are flat membranes from PolyAn which carry hydrophobic functional groups and are referred to as HIC membranes. The effect of the hydrophobic ligand on binding is, however, low, and the binding capacity is only up to 1.8 times higher in comparison with the base membrane (i.e., membrane without ligand).

To date, membranes for hydrophobic interaction chromatography, i.e., HIC applications, have not become prevalent on an industrial scale. The macroporous, flat membranes which are known in the prior art and which are modified with hydrophobic ligands do not exhibit sufficient binding capacities.

The coating of macroporous support structures with a ligand-carrying polymer layer has gained acceptance for ion-exchange membranes. The ionic groups in the pores of the ion-exchange membranes repel one another at low ionic strengths so that a three-dimensional hydrogel structure can form in the pores of the support. This effect, also known as the polyelectrolyte effect, does not occur in the case of hydrophobic ligands. The hydrophobic layer collapses at high ionic strengths, preventing the formation of the three-dimensional structure (see E. Müller, Chem. Eng. Technol. 2005, 28, No. 11). Thus, it has not been possible to date to achieve high binding capacities, as are known for ion-exchange membranes, with hydrophobic ligands or affinity ligands as well.

Accordingly, it is therefore an object of the present invention to provide flat adsorbents, i.e., membranes having improved properties, more particularly having a higher binding capacity for hydrophobic interaction chromatography, and also to specify an inexpensive and environmentally friendly method for producing such adsorbents.

These objects are achieved by the subject matter characterized in the claims.

The present invention thus provides separation materials, i.e., adsorbents, for hydrophobic interaction chromatography on the basis of flat or flat-shaped porous base supports (membranes) on whose surface functional groups are immobilized, i.e., hydrophobic ligands which are capable of entering into interactions with adsorbates present in fluids.

The membrane according to the invention comprises a cellulose hydrate matrix having pores which stretch from one main surface of the membrane to the other main surface of the membrane, wherein the membrane is crosslinked and has functional groups in the form of hydrophobic ligands on its inner and outer surfaces. Main surfaces shall be understood to mean the outer surfaces of a membrane.

The pore structure of the membrane according to the invention, through the low dependence of the flow rate on the ionic strength of the medium, appears to be a hybrid of aerogel and xerogel, similar to crosslinked agarose gels. This is consistent with the fact that the introduction of hydrophobic ligands also leads to an effective adsorption membrane for hydrophobic interaction chromatography (HIC), as shown in the examples of the present invention. More particularly, it has become apparent that, unforeseeably, the membrane according to the invention does not collapse even at high ionic strengths and the three-dimensional structure thus remains preserved, as a result of which the separation capacity of the membrane is distinctly improved.

A starting material used for the adsorption membrane according to the invention is a cellulose ester membrane which is contacted with at least one solution under conditions which lead firstly to swelling of the cellulose ester matrix and secondly, at the same time, i.e., in situ, to hydrolysis of the ester groups to hydroxyl groups, resulting in a cellulose hydrate membrane.

The swelling of the cellulose ester matrix during the hydrolysis of the ester groups is described by the degree of swelling, i.e., the ratio of the water permeability of the cellulose ester membrane wetted beforehand with water to the water permeability of the final, i.e., hydrolyzed, cellulose hydrate membrane, which has been activatingly crosslinked and optionally provided with ligand(s).

Subsequent to the hydrolysis, the cellulose hydrate matrix obtained is preferably crosslinked by reacting the hydroxyl groups with one or more at least bifunctional reagents, and functional groups (ligands) for enabling adsorptive material separation are then introduced into the crosslinked matrix.

Figure 4:
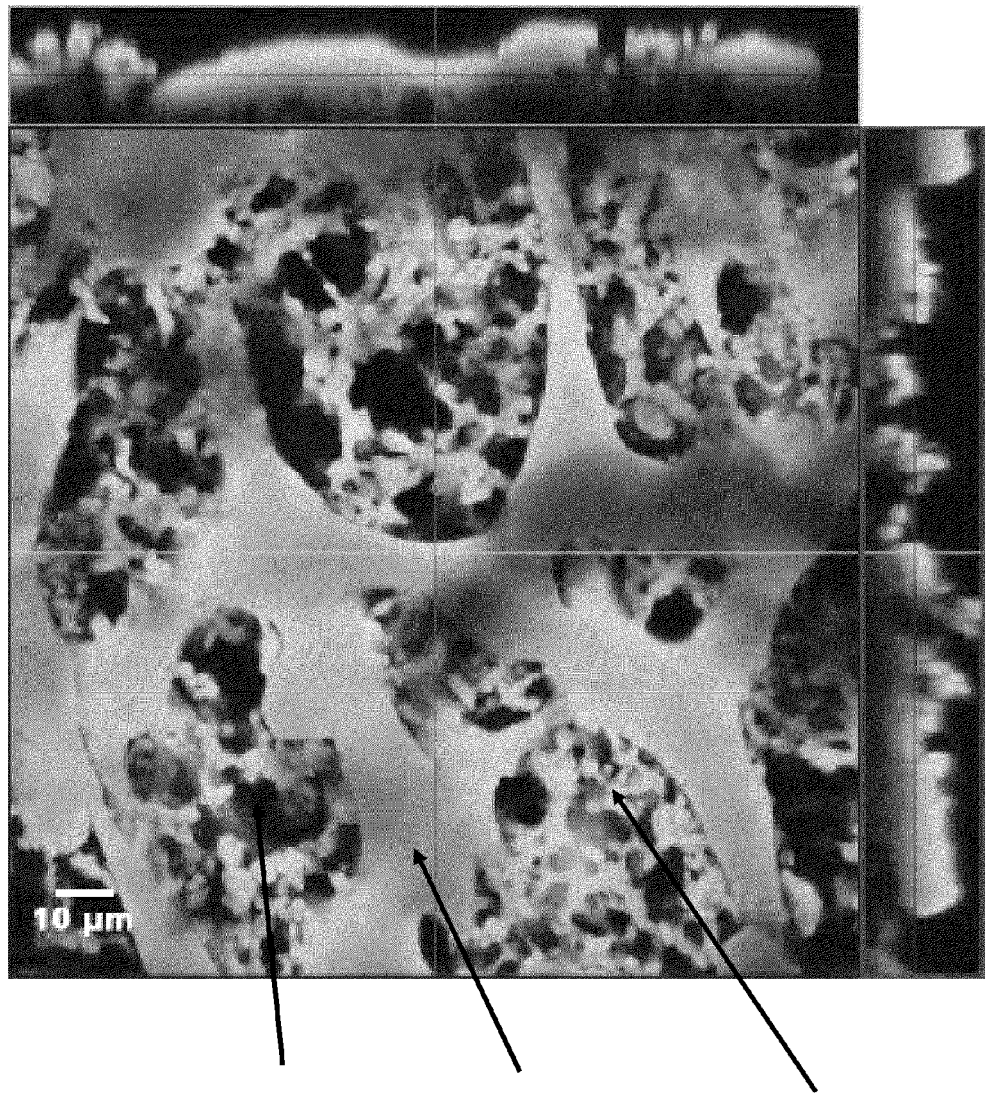

It was found that, surprisingly, the binding capacity of the cellulose hydrate membrane is distinctly increased when the hydrolysis step is carried out under conditions under which the cellulose can swell. The increase in the binding capacity for biomolecules may possibly be caused by the increased number of amorphous regions accessible to biomolecules in the cellulose. Swelling the cellulose support results in two types of pores: a) micropores having a diameter of >100 nm, which are generally smaller than the original pores of the cellulose ester membrane, and b) ultrapores (amorphous regions of the cellulose) having a diameter of <100 nm, which are shaped such that they are not accessible to Blue Dextran (available as Blue Dextran molecular weight 2 000 000 from Sigma, St. Louis, Mo., USA, product number D5751, CAS number: 87915-38-6) and which offer an additional adsorption surface accessible to ligands and adsorbates (cf. FIG. 1c). The effectiveness of adsorption of the membrane according to the invention is not restricted to the phase boundary of the connected micropores with the medium, but extends at least to a portion or even the entire volume in the ultrapores of the support (see FIG. 4). FIG. 4 shows a confocal micrograph of a lysozyme-laden membrane according to the invention having ultrapores. In order to be able to better explain and illustrate the different influences of the production process on the properties of the membranes according to the invention, both hydrophobic ligands and ionic ligands were used in the examples.

The swelling of the cellulose during the hydrolysis can be affected and controlled by a suitable pretreatment of the cellulose ester or by the parameters for hydrolysis (composition of the hydrolysis medium, type of additive, concentration of the additive, hydrolysis temperature). Thus, the permeability and capacity of the membrane can be adjusted. The adsorptive cellulose hydrate membranes produced in the method according to the invention show, compared to the cellulose hydrate membranes produced by production methods known in the field, distinctly higher binding capacities with comparable permeabilities.

As will be described hereinafter, the method for producing the membrane according to the invention can be carried out in three steps, wherein the setting of the desired degree of swelling, of the flow rate, and of the binding capacity can be controlled both by the parameters for the pretreatment (type of additive, concentration of the additive, pretreatment temperature) and the parameters for the hydrolysis (composition of the hydrolysis medium, type of additive, concentration of the additive, hydrolysis temperature). The membrane according to the invention can also be produced without pretreatment of the cellulose ester matrix. High degrees of swelling of the cellulose hydrate matrix can be achieved by the method according to the invention through a high concentration of alkali metal hydroxide in the hydrolysis medium, a high concentration of hydrogen-bond-breaking compounds, or a low temperature of the hydrolysis medium.

Through the type of crosslinking agent, the concentration of the crosslinking agent, the concentration of the crosslinking catalyst, the duration of crosslinking, optionally the type and concentration of an inert organic solvent and/or the crosslinking temperature, it is possible to control the degree of crosslinking, the pore size, and the number of residual active groups, e.g., epoxide groups. As a result, the activation often necessary for the bonding of the functional groups can take place as early as in the crosslinking step.

In a further step, functional groups are bonded, for example, to the hydroxyl groups of the crosslinked membrane. Techniques for bonding functional groups are known per se to a person skilled in the art (e.g., from Greg T. Hermanson, A. Krishna Mallia, Paul K. Smith, Immobilized Affinity Ligand Techniques, Academic Press, INC, 1992).

Preferably, functional groups are bonded to the cellulose membrane via epoxide groups or aldehyde groups. The introduction of the epoxide groups can take place in the crosslinking step or afterwards.

The combinations of the influencing factors (a) of the production conditions of the cellulose ester membrane used as a starting material, (b) of the conditions of any pretreatment carried out, (c) of the hydrolysis conditions, and (d) of the crosslinking conditions of the cellulose ester membrane also make it possible to produce multiple different end products from one starting membrane, resulting in a considerable simplification in terms of production technology.

Starting Membrane

The cellulose ester membrane used as a starting membrane in the method according to the invention has a pore size in the range from 0.1 to 20 µm, preferably from 0.5 to 15 µm, and more preferably from 1 to 10 μm, and is produced by a customary production method known in the field. To determine the pore size, a "capillary flow porometry test" is carried out. Further details can be found in the operating instructions (Capillary Flow Porometer 6.0, CAPWIN Software System, Porous Materials Inc.). Cellulose ester membranes can be composed of cellulose monoacetate, cellulose diacetate, cellulose triacetate, cellulose propionate, cellulose butyrate and cellulose acetobutyrate or other suitable cellulose esters, or cellulose nitrate, methylcellulose or ethylcellulose, and also mixtures thereof, preference being given to cellulose acetates, more particularly cellulose diacetate. It is known to a person skilled in the art that the cellulose ester membrane can, in part, also contain hydroxyl groups in addition to the ester groups.

Pretreatment

Before the hydrolysis, the cellulose ester membrane can be pretreated in a suitable medium. The temperature in the pretreatment step is preferably in a range from 20 to 100° C., particular preference being given to a temperature in a range from about 60° C. to about 80° C. A gas, such as, for example, air, an organic solvent, such as, for example, an alcohol, or an aqueous medium can be used as a pretreatment medium, preference being given to an aqueous medium. The pretreatment medium comprises preferably one or more additives which have a dissolving or plasticizing effect on a cellulose ester. Suitable additives are, in particular, acids, more particularly carboxylic acids, such as acetic acid, and water-soluble plasticizers for cellulose esters, such as diacetin, triacetin, and sulfolane. However, it is particularly preferred, in particular for commercial reasons, to use acetic acid as an additive for the pretreatment medium; although diacetin and triacetin also deliver excellent results, they are more expensive. The concentration of the additive in the pretreatment medium is not subject to any particular restrictions.

The duration of the pretreatment has no substantial influence on the pretreatment effect, provided that a minimum exposure time is applied which ensures a temperature equalization of the cellulose ester membrane in the pretreatment medium and a concentration equalization of any additive used in the membrane. The upper limit of the exposure time of the pretreatment medium is determined by the time from which a chemical reaction of the cellulose ester membrane with the pretreatment medium, for example by hydrolysis, could occur. In other words, the exposure time of the pretreatment medium is set such that no (premature) hydrolysis of the pretreated cellulose ester membrane occurs. Usually, the exposure time of the pretreatment medium to the cellulose ester starting membrane is between 0.1 second and 1 hour, preference being given to an exposure time in the range from 10 seconds to 10 minutes. The extent of the pretreatment effect is dependent on the highest temperature in conjunction with the highest concentration of the additive which affect the cellulose ester membrane. Thus, when the cooling or rinsing-out of the additive takes place over a longer period, this has no influence on the pretreatment effect already achieved. The pretreatment can therefore be terminated by rinsing the pretreatment additive out of the membrane and/or lowering the temperature of the pretreatment medium.

Hydrolysis

The optionally pretreated cellulose ester membrane is hydrolyzed with a suitable hydrolysis medium, whereby the cellulose hydrate membrane forms by swelling of the cellulose matrix. Depending on the type of pretreatment medium, the cellulose ester membrane can be used dry or wet in the hydrolysis step.

Through the swelling of the cellulose, the accessibility of the hydroxyl groups for the attachment of the functional groups and subsequently for the adsorbates is improved. The hydrolysis of the cellulose ester membrane is preferably carried out in an aqueous medium. More preferably, an aqueous hydrolysis medium having a pH of >7, i.e., a basic medium, is used. The hydrolysis medium comprises preferably an alkaline compound, preferably an alkali metal hydroxide. It is particularly preferred to use an aqueous solution of sodium hydroxide or lithium hydroxide. Use can also be made of mixtures of one alkali metal hydroxide and other alkaline compounds, such as alkali metal carbonate, such as sodium carbonate, potassium carbonate, cesium carbonate, sodium hydrogen carbonate, and/or sodium triphosphate, potassium triphosphate, sodium silicate and potassium silicate.

The concentration of the alkaline compound in the hydrolysis medium can be up to about 50% by weight, preference being given to a concentration in the range from 0.1 to 50% by weight and particular preference to a concentration in the range from 0.4 to 10% by weight. In a particularly preferred embodiment of the present invention, a hydrolysis medium composed of water and sodium hydroxide is used, the concentration of the sodium hydroxide in the hydrolysis medium being preferably in a range from 0.1 to 20% by weight, particularly preferably in a range from 0.4 to 4% by weight.

The hydrolysis medium can comprise one or more additives which have a swelling-influencing effect on a cellulose ester. Suitable additives are, in particular, salts, such as sodium chloride, sodium sulfate, and sodium acetate, hydrogen-bond-breaking compounds, such as urea, or organic solvents, such as ethylamine. The organic solvent is preferably selected from the group consisting of alcohols, ketones, and ethers. Particularly preferred solvents are ethanol, methanol, ethylene glycol, propylene glycol, glycerol, acetone, dioxane, or diglyme. The additive in the hydrolysis medium should influence the swelling, but not completely suppress it.

The temperature of the medium used in the hydrolysis step can be in the range from about 10° C. up to the boiling point of the hydrolysis medium, preference being given to a temperature in a range from 15° C. to about 25° C.

The duration of hydrolysis is determined by the composition of the hydrolysis medium and the hydrolysis temperature. Usually, the duration of hydrolysis is in the range from 0.1 to 60 minutes, preference being given to a duration of hydrolysis in the range from 5 to 45 minutes. A particularly preferred duration of hydrolysis in the range from 20 to 40 minutes.

Crosslinking

The cellulose hydrate membrane obtained following any pretreatment carried out and following the hydrolysis with swelling is crosslinked with a crosslinking agent to increase the chemical resistance of the membrane and/or to introduce functional groups.

The crosslinking agent has at least two functional groups in the molecule which are reactive with the hydroxyl groups of cellulose and thus make crosslinking of cellulose possible. The usable crosslinking agents are, in principle, not subject to any particular restrictions and a person skilled in the art is capable of selecting them from a series of crosslinking agents usable for the crosslinking of cellulose. However, it is preferred to use, in the crosslinking step, a diepoxide compound or else other compounds which are reactive with hydroxyl groups of cellulose and have at least two reactive functional groups, such as diisocyanate, epichlorohydrin, epibromohydrin, dimethylurea, dimethylethyleneurea, dimethylchlorosilane, bis(2-hydroxyethyl) sulfone, divinyl sulfone, alkylene dihalogen, hydroxyalkylene dihalogen, and glycidyl ethers.

From the group of the glycidyl ethers, preference is given to 1,4-butanediol diglycidyl ether, ethylene glycol diglycidyl ether, glycerol diglycidyl ether, and polyethylene glycol diglycidyl ether.

Particular preference is given to the use of 1,4-butanediol diglycidyl ether or epichlorohydrin as a crosslinking agent.

Optionally, a mixture of different crosslinking agents can be used.

The crosslinking can take place in an aqueous medium, in an organic solvent, or else in a mixture of water and an organic solvent. Preferably, the crosslinking is carried out in an aqueous medium.

It is further preferred to use a crosslinking catalyst, such as sodium hydroxide, to accelerate the crosslinking of cellulose with the crosslinking agent.

The temperature of the medium used in the crosslinking step can be in the range from about 4° C. up to the boiling point of the crosslinking medium, preference being given to a temperature in a range from 5° C. to about 70° C. A particularly preferred temperature is in the range from 20° C. to 40° C.

Usually, the duration of crosslinking is in the range from 10 minutes to 100 hours, preference being given to a duration of crosslinking in the range from 30 minutes to 48 hours. A particularly preferred duration of crosslinking is in the range from 2 to 24 hours.

As described above, the method for producing the membrane according to the invention can be carried out in three steps, wherein the setting of the desired degree of swelling of the matrix can be controlled both by the parameters for the pretreatment (type of additive, concentration of the additive, pretreatment temperature) and the parameters for the hydrolysis (composition of the hydrolysis medium, type of additive, concentration of the additive, hydrolysis temperature). The membrane according to the invention can also be produced without pretreatment.

Activation and Bonding of Functional Groups

In a further step, functional groups, i.e., hydrophobic ligands, are bonded to the hydroxyl groups of the crosslinked cellulose hydrate membrane. Techniques for bonding functional groups are known to a person skilled in the art (e.g., from Greg T. Hermanson, A. Krishna Mallia, Paul K. Smith, Immobilized Affinity Ligand Techniques, Academic Press, INC, 1992).

A customary method for introducing functional groups is based on reacting the membrane, which is activated with oxirane groups, with an alcohol in the presence of boron trifluoride etherate. Other production methods are based on reacting a hydroxyl-group-containing support with an oxirane-group-containing molecule in the presence of boron trifluoride etherate. Other methods are based on reacting oxirane-containing activated supports with amines.

Preferably, the hydrophobic ligands are bonded to the cellulose membrane via epoxide groups or aldehyde groups. The epoxide activation can take place as early as in the crosslinking step or afterwards.

It is also possible to introduce the hydrophobic ligands during the crosslinking, e.g., by adding an amine and/or a monofunctional epoxide compound, such as phenyl glycidyl ether or butyl glycidyl ether, to a diepoxide compound.

The functional groups for the membrane according to the invention are selected from: $C_1$-$C_{20}$-alkyl and their derivatives or $C_6$-$C_{25}$-aryl and their derivatives or $C_7$-$C_{25}$-arylalkyl and their derivatives or —$[(CH_2)_m$—O—$]_n$—R, where m is 2 or 3, n is a whole number greater than 1, and R is —H or —$C_1$-$C_5$-alkyl.

The membranes according to the invention can, after the introduction of the ligands, optionally be dried. Membranes can be directly dried to remove water or organic solvents, preferably alcohol, or can be dried after carrying out a stepwise replacement of water with an organic solvent. Preferably, the membranes are dried to remove a medium which comprises a pore-stabilizing compound. Particularly preferably, the membranes according to the invention are dried to remove an aqueous glycerol solution. The concentration of the glycerol is preferably in the range from 5 to 40% by weight, based on the aqueous solution.

EXPLANATION OF THE EXAMPLES

Crosslinked cellulose hydrate membranes having a low degree of swelling are, for example, produced from cellulose ester membranes hydrolyzed with ethanolic potassium hydroxide solution. A cellulose acetate membrane yields, in this way, a crosslinked cellulose hydrate membrane which has a negligibly lower flow rate (see example 1), but which has, after introduction of ligands, virtually no adsorption capacity (binding capacity) (see table 5).

It has now been found that, although hydrolysis with an aqueous sodium hydroxide solution lowers the flow rate (see example 2), distinctly increased binding capacities occur following overlaying with various ligands, increasing sodium hydroxide solution concentrations resulting in a stronger flow rate reduction and higher binding capacities (see table 5). Compared with the membrane-penetrating micropores which mainly form in the hydrolysis with ethanolic potassium hydroxide solution, the formation of a multiplicity of small ultrapores seems to be preferred in the hydrolysis with aqueous sodium hydroxide solution. A higher hydrolysis temperature and also an additional content of electrolytes, including sodium acetate already formed in the hydrolysis, have the same effect as a lower sodium hydroxide solution concentration.

WO 2007/017085 A2 describes a method for producing crosslinked cellulose hydrate membranes, which consists in the simultaneous hydrolysis and crosslinking of cellulose ester membranes and is intended to be equally suitable for filtration and adsorption membranes. One of the goals of the invention described therein is the hydrolysis and crosslinking of the cellulose ester under conditions which do not affect the structure and permeability of the membrane. Through simultaneous hydrolysis and crosslinking under conditions which suppress swelling and structural change ($Na_2SO_4$, low sodium hydroxide solution concentration), no significant binding capacity is found (see comparative example 1). Only when the alkaline solution concentration is increased is there an increase in the binding capacity. However, the swelling of the cellulose here also leads to a change in the pore structure, contrary to the simultaneous hydrolysis and crosslinking process described in the prior art. The binding capacity here is, however, only about 5% of the binding capacity in comparison with the hydrolysis and crosslinking carried out separately (see example 2 and comparative example 1).

Furthermore, it has been found that different pretreatment of the cellulose acetate membrane has different effects on the properties of the adsorptive membrane according to the invention. The flow rate decreases and the binding capacity increases when the cellulose acetate membrane has been heated to 80° C. under air prior to the hydrolysis (see example 3). When the cellulose acetate membrane is heated to 80° C. in 20% acetic acid prior to the hydrolysis (see example 4), the flow rate increases in comparison with the non-pretreated membrane from example 2 and the binding capacity changes depending on the size of the protein. The binding capacity increases for lysozyme (14.3 kDa); the binding capacity decreases for bovine serum albumin (BSA; 60 kDa) and gamma-globulin (150 kDa). The pretreatment can, for example, be advantageous in specific separation tasks when solely the specificity of the ligand is not sufficient for material separation, and the molar masses of the components to be separated are so different that the overall result of superimposing a size-exclusion effect on purely adsorptive material separation is an improvement in the separation capacity, and the influencing of the pore size of the ultrapores through choice of base and its concentration needs support. A complete separation solely on the basis of this effect is, however, not possible because the size exclusion only becomes effective for the adsorption on the inner surface of the ultrapores, but not on the outer surface of the micropores.

These findings indicate, in the case of hydrolysis and crosslinking of cellulose acetates, complex swelling and deswelling procedures whose effects with regard to the structure of the end product are difficult to summarize because there are both procedures in which a flow rate reduction is coupled with an increase in the binding capacity and procedures in which this is not the case. The former are referred to hereinafter as "productive", the others as "unproductive". The pretreatment of the cellulose acetate membrane has different effects on the change in pore structure, and the formation of micropores and also of ultrapores. It is thus possible, through a suitable choice of the pretreatment, to influence the flow rate, the binding capacity but also the size exclusion of the adsorptive membrane according to the invention. The main goal of the method according to the invention is the restriction to productive flow rate reductions, which should take account not only of the swelling behavior of the starting material, the cellulose acetate membrane, and the end product, the crosslinked cellulose hydrate membrane, but also the entire spectrum of the intermediate products in the partially hydrolyzed and partially crosslinked state. For example, it is known that cellulose acetates of decreasing acetyl content even pass through, in a narrow range, a state of water solubility.

According to the invention, a cellulose ester membrane is sequentially hydrolyzed in a swelling medium, preferably an aqueous solution of an alkali metal hydroxide, crosslinked with an at least bifunctional agent, and provided with an adsorption-effective ligand. The swelling capacity of the alkali metal hydroxides increases with smaller cation radii and higher concentrations (see example 5).

The cellulose is preferably crosslinked according to the invention with 1,4-butanediol diglycidyl ether. In an embodiment of the invention, the cellulose is crosslinked with 1,4-butanediol diglycidyl ether such that, because of a partly one-sided reaction, a sufficient number of unreacted epoxide groups are preserved ("activating crosslinking", see example 2) and can serve to bond or to couple or to construct ligands. The unreacted epoxide groups are relatively hydrolysis-stable and were used for subsequent reactions even after humid storage at room temperature for up to 24 hours. In another embodiment of the invention for bonding "active" ligands, the crosslinking is carried out under more severe conditions (longer duration of crosslinking and/or higher alkali concentration and/or higher temperature) so that, with increased reaction with the cellulose and/or increased hydrolysis of the surplus groups, virtually no epoxide groups remain ("nonactivating crosslinking", see example 6). Remaining epoxide groups can also be hydrolyzed by subsequent treatment with, for example, 5% sulfuric acid at elevated temperature.

The flow rate of the membrane according to the invention in example 2 for a 20 mM Tris/HCl buffer with a pH of 7.3 is 8% greater than that for pure water. Corresponding values for adsorption membranes which were produced by coating according to the prior art are in the range from 20%, in the case of a crosslinked auxiliary polymer, to 200%, in the case of an uncrosslinked auxiliary polymer. The resulting pore structure, by virtue of the low dependence of the flow rate on the ionic strength of the medium, appears to be a hybrid of aerogel and xerogel, similar to a crosslinked agarose gel. This is consistent with the fact that the introduction of hydrophobic ligands also leads to an effective adsorption membrane for hydrophobic interaction chromatography (HIC) (see examples 4 and 9).

It is difficult to distinguish the adsorption membranes according to the invention from adsorption membranes produced by polymer coating or grafting according to the prior art by scanning electron microscopy because its resolution would be overwhelmed by the small-pored structures (i.e., ultrapores) which constitute the main difference. In contrast, the characterization of adsorptive membranes by means of confocal laser scanning microscopy (CLSM) simultaneously delivers, under suitable conditions, information both about the pore structure and about the distribution of protein bound to functional groups in the membrane. For this purpose, the membrane material and protein have to be labeled with two different fluorescent dyes. All microscopic measurements were carried out at approximately the same distance (about 20 µm) from the respective outer surface. In all cases, three independent measurements at different x,y-positions led to very similar results characteristic of the respective membrane type.

Characteristic of all membrane samples is a very coarse structure (dark areas in FIGS. 2-4) composed of relatively thick fibers or their agglomerates interspersed with more finely distributed fibroid or clusterlike membrane material with completely or partially undyed areas which can be attributed to the membrane-penetrating micropores having dimensions of up to about 20 µm. The protein distribution was clearly identifiable for all membrane samples. However, very great differences with regard to protein amount (fluorescence intensity, bright areas) and protein distribution in the pore structure (dark areas) were found. The total fluorescence intensities were distinctly different; for the membrane according to the invention in example 2, it was even necessary to select a lower amplification than for the other membranes: Membrane from Example 2>Sartobind® S Membrane>>Membrane from Example 1

These results correlate well with the figures for the binding capacity:
Membrane according to example 1: 0.01 mg/cm$^2$
Sartobind® S membrane: 0.90 mg/cm$^2$
Membrane according to example 2: 2.06 mg/cm$^2$ Using the investigative technique, it was possible to identify clear and great differences with regard to protein binding between the established Sartobind® S membrane (FIG. 2) and the membranes functionalized with sulfonic acid ligands from example 1 (FIG. 3) and example 2 (FIG. 4). With the membranes from examples 1 and 2, the fluorescence intensities for the protein (bright areas) correlate with the nominal protein-binding capacities, i.e., the membrane from example 1 exhibits only a very low binding capacity, while the membrane according to the invention from example 2 exhibits a distinctly higher binding capacity.

The protein in the Sartobind® S membranes, based on the same pore structure of the base support, binds, in particular, in the volume of the micropores, a three-dimensional functional layer being essential for the protein binding. These membranes show, at the edges of the pores, sharp boundaries between the material of the membrane (dark areas) and the protein layer (bright areas). Because of the restricted range of this functional layer, small fractions of the pore volume remain in which no protein is bound. In the case of the membrane from example 1, the binding takes place directly on the membrane material, recognizable by small, bright points in FIG. 2. In contrast to this, in the case of the membrane according to the invention from example 2, clearly very large amounts of protein are bound in the ultrapores of the coarse fiber structure and also in the more finely distributed fibroid or clusterlike membrane material. Between the distributions of cellulose and protein, a very good correlation is found, also recognizable visually from the fact that only the mixed color of the dyes used is recognizable in the overlay, because both pore surface and protein are visible in the depth of the ultrapores. By far the largest fraction of the volume of the micropores contains no protein.

In order to quantify the ultrapores of the membranes according to the invention, an experiment was carried out in which the accessibility of the pores to Blue Dextran was determined. The experiment was carried out in the manner described in example 14. The result of the evaluation is shown in table 1 and in FIG. 5.

Figure 5:
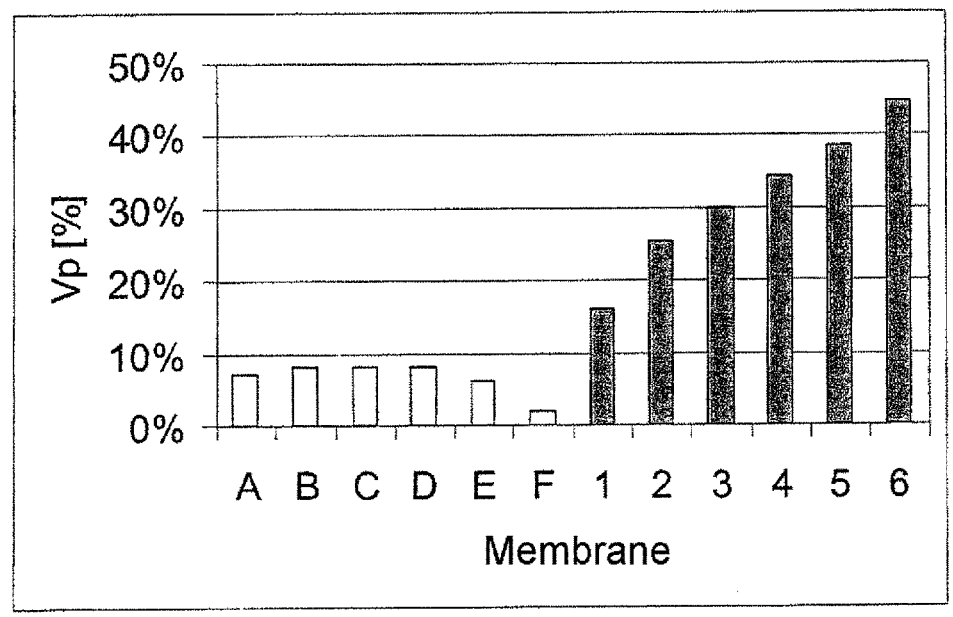

In FIG. 5, a distinct difference is recognizable between the ultrapores inaccessible to Blue Dextran for the membranes A-F known in the prior art and membranes according to the invention from example 14. In the case of the membranes according to the invention, which were hydrolyzed under swelling conditions, more than 15% of the entire pore volume is in the range of ultrapores (i.e., pores having a diameter <100 nm which are not accessible to Blue Dextran), whereas it is less than 8% for the comparative membranes A-F.

Accordingly, membranes according to the invention have a volume of ultrapores which are accessible to water, but not to Blue Dextran having a molecular weight Mw of 2 000 000, of more than 15%, preferably more than 18%, more preferably more than 20%, even more preferably more than 25%, and most preferably more than 30% of the entire pore volume.

FIGURES

FIG. 1a): Schematic illustration of the binding of protein to micropores of an adsorptive membrane known in the prior art and produced as in example 1.

FIG. 1b): Schematic illustration of the binding of protein to an adsorptively active polymer coating of adsorptive membranes as described in the prior art which consist of one or more support structures and one or more adsorptively active polymer coatings.

FIG. 1c): Schematic illustration of the binding of protein in the ultrapores of an adsorptive membrane according to the invention.

Figure 2:
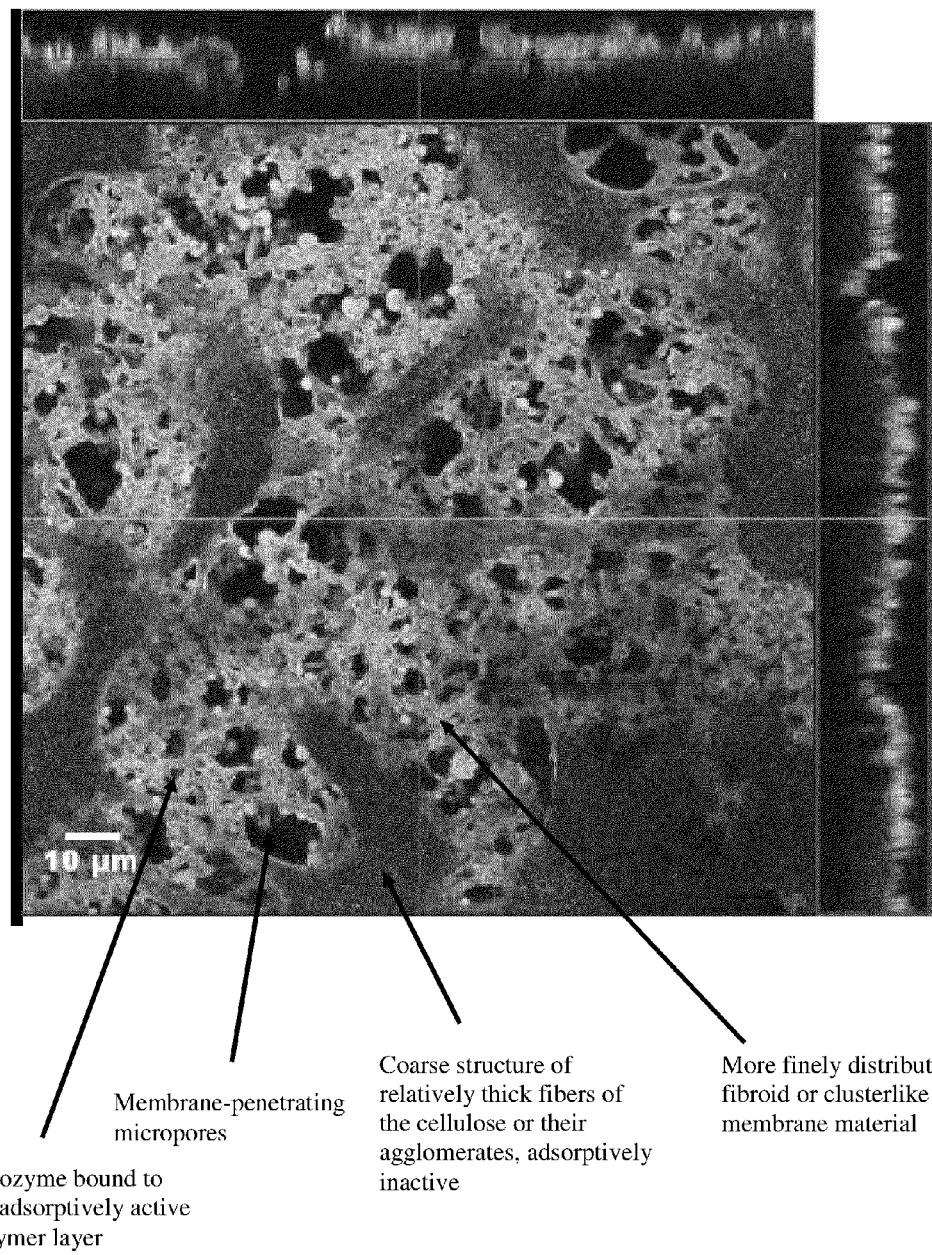

FIG. 2: CLSM image of the pore morphology and protein distribution on the upper side of the Sartobind® S membrane following labeling of the cellulose with fluorescent dye and loading with fluorescently labeled lysozyme.

Figure 3:
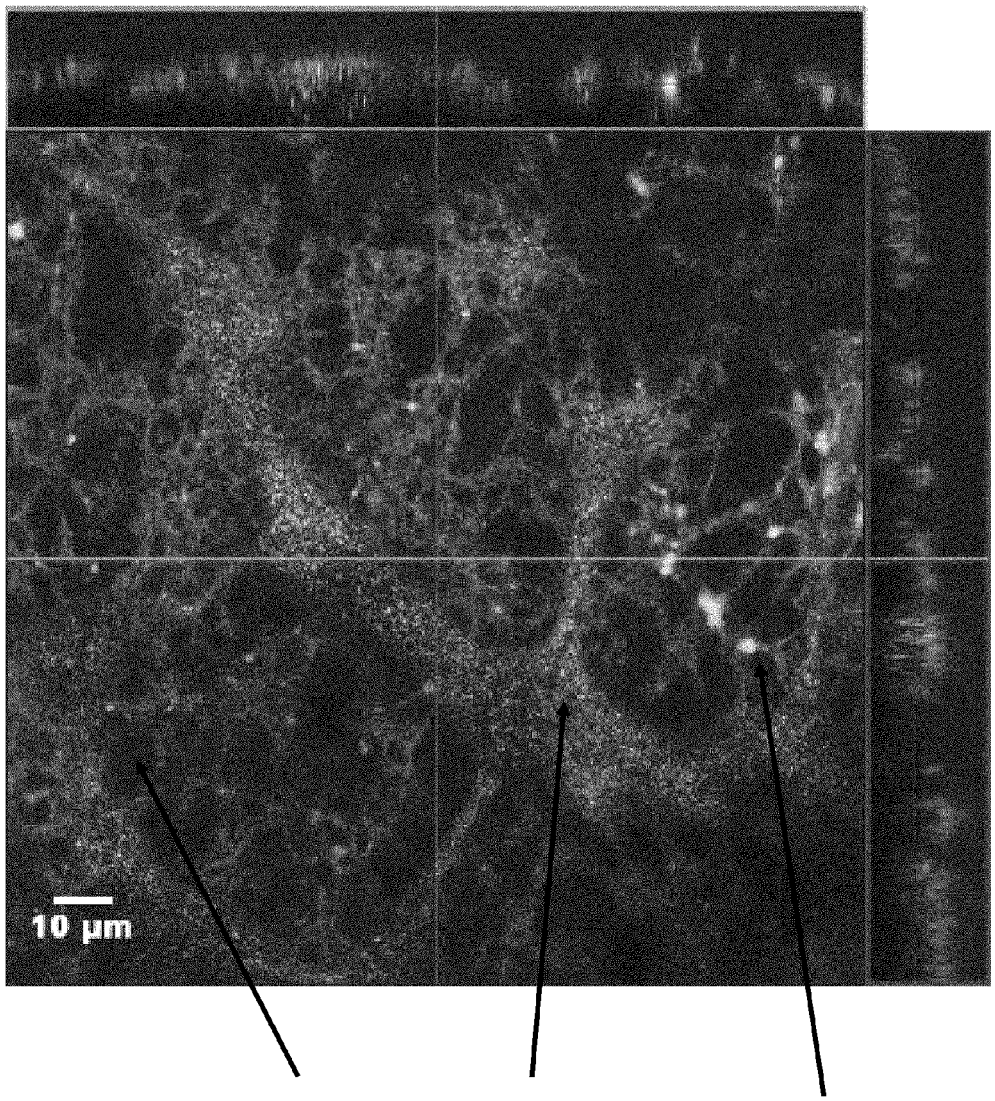

FIG. 3: CLSM image of the pore morphology and protein distribution on the upper side of the membrane reacted with sulfonic acid ligands according to example 1 following labeling of the cellulose with fluorescent dye and loading with fluorescently labeled lysozyme.

FIG. 4: CLSM image of the pore morphology and protein distribution on the upper side of the membrane reacted with sulfonic acid ligands according to example 2 following labeling of the cellulose with fluorescent dye and loading with fluorescently labeled lysozyme.

FIG. 5: Comparison of the percentage of pores inaccessible to Blue Dextran having a molecular weight Mw of 2 000 000 in the membranes:
A: Membrane from example 1
B-F: Cellulose membranes according to the prior art, 0.2-0.45 μm, from Sartorius Stedim Biotech GmbH
1-6: Membranes according to the invention from example 14

FIG. 6: Protein separation according to example 15 with a membrane having butyl ligands (butyl membrane).

FIG. 7: Protein separation according to example 15 with a membrane having phenyl ligands (phenyl membrane).

FIG. 8: Protein separation according to example 15 with a membrane having hexyl ligands (hexyl membrane).

FIG. 9: Protein separation according to example 15 with a membrane having octyl ligands (octyl membrane).

Figure 10:
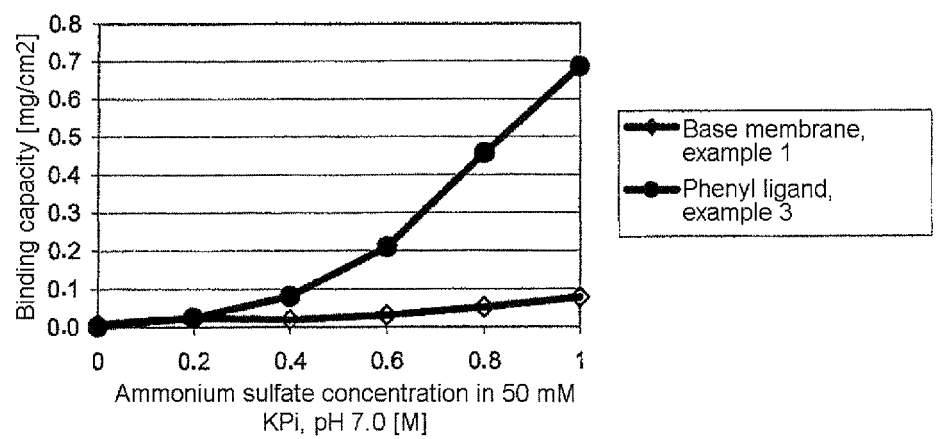

FIG. 10: Dependence of the binding capacity of a membrane produced as in example 9 and having phenyl ligands (phenyl membrane) on the ammonium sulfate concentration in the filter medium.

EXAMPLES

All mention in the examples of a CA membrane refers to a polyester-nonwoven-reinforced type of cellulose acetate membrane having a pore diameter of about 3 μm (measured with a Coulter Capillary Flow Porometer 6.0, CAPWIN Software System, Porous Materials Inc.), which has a water flow rate of 730 ml/(min×bar×cm$^2$). The thickness of the modified membrane samples was, on average, 250 μm. All flow rate figures are in ml/(min×bar×cm$^2$), and all binding capacity figures are in mg/cm$^2$. Unless stated otherwise, percentages are based on weight.

Example 1

Activatingly Crosslinked Cellulose Hydrate Membrane Having a Low Degree of Swelling for Comparative Examples The membrane was produced in the following way: A CA membrane, as mentioned above, was used as starting material. This CA membrane was hydrolyzed for three minutes at room temperature with a 15% potassium hydroxide solution in 80% ethanol. Subsequently, it was rinsed for three minutes with a 6.8% acetic acid solution, twice with ethanol, and then for 15 minutes with running reverse-osmosis (RO) water. Afterwards, the membrane was dried for 20 minutes at 80° C. in a circulating air drying cabinet.

In the next step, the dried membrane thus obtained was treated for 30 minutes at room temperature with 30% 1,4-butanediol diglycidyl ether in an aqueous 0.1 M sodium hydroxide solution and aqueous 0.1% sodium borohydride solution, and then the moist membrane was left to stand for 20 hours in a closed vessel at room temperature.

Finally, the membrane was rinsed for 30 minutes with running water.

The water flow rate of the activatingly crosslinked cellulose hydrate membrane thus produced was 630 ml/(min×bar× cm$^2$). The degree of swelling was 1.16.

Example 2

Activatingly Crosslinked Intermediate Product for an Adsorption Membrane According to the Invention A CA membrane, as in example 1, was used as starting material. This CA membrane was hydrolyzed for 30 minutes at room temperature with a 0.6 M aqueous sodium hydroxide solution (i.e., under swelling conditions) and subsequently rinsed for 3×10 minutes with a 0.5 M aqueous sodium hydroxide solution. The membrane obtained was treated (i.e., crosslinked) for 30 minutes at room temperature with 30% 1,4-butanediol diglycidyl ether in a 0.1 M aqueous sodium hydroxide solution and 0.1% aqueous sodium borohydride solution, and then the moist membrane was left to stand for 20 hours in a closed vessel at room temperature.

Finally, it was rinsed for 30 minutes with running water.

The water flow rate of the activatingly crosslinked intermediate product was 45 ml/(min×bar×cm$^2$), and the degree of swelling was 16.2.

Example 3

Activatingly Crosslinked Intermediate Product for an Adsorption Membrane According to the Invention: Pretreatment of the CA Membrane A CA membrane was treated in the same way as in example 2, with the exception that the CA membrane was heated for 20 minutes at 80° C. in the drying cabinet prior to the hydrolysis.

The water flow rate of the resulting activatingly crosslinked intermediate product was 21 ml/(min×bar×cm$^2$), and the degree of swelling was 34.8.

Example 4

Activatingly Crosslinked Intermediate Product for an Adsorption Membrane According to the Invention: Pretreatment of the CA Membrane A CA membrane was treated in the same way as in example 2, with the exception that the CA membrane, prior to the hydrolysis, was heated in a 20% acetic acid solution to 80° C. and rinsed for 15 minutes with running water.

The water flow rate of the resulting activatingly crosslinked intermediate product was 180 ml/(min×bar×cm$^2$), and the degree of swelling was 4.06.

Example 5

Various Alkali Hydroxides

CA membranes were, in each case, hydrolyzed in 0.5 M aqueous solutions of LiON, NaOH, and KOH for 30 minutes at room temperature, and subsequently, without rinsing, crosslinked for 3.5 hours at room temperature with aqueous solutions of 15% 1,4-butanediol diglycidyl ether and 0.1% sodium borohydride solution in the same alkali metal hydroxide solutions. The membranes were further reacted with a quaternary ammonium ligand by treating the crosslinked membranes for 35 minutes at 30° C. in a 10% aqueous solution of trimethylamine and for 5 minutes at room temperature in a 5% sulfuric acid solution and then rinsing them for 10 minutes with running water. The results are reported in table 5.

Example 6

Nonactivatingly Crosslinked Intermediate Product for Adsorption Membrane According to the Invention A CA membrane, as in example 1, was used as a starting membrane. This CA membrane was hydrolyzed for 30 minutes at room temperature with a 0.6 M aqueous sodium hydroxide solution and subsequently rinsed for 3×10 minutes with a 0.5 M aqueous sodium hydroxide solution. The membrane obtained was treated (crosslinked) for 30 minutes at room temperature with aqueous 15% 1,4-butanediol diglycidyl ether in a 0.5 M aqueous sodium hydroxide solution and 0.1% aqueous sodium borohydride solution, and then the moist membrane was left to stand for 20 hours in a closed vessel at room temperature. Finally, it was rinsed for 30 minutes with running water.

The water flow rate of the nonactivatingly crosslinked intermediate product was 31 ml/(min×bar×cm$^2$), and the degree of swelling was 23.5.

Example 7

Introduction of Quaternary Ammonium Ligands (Q Membrane)

Activatingly crosslinked membranes (intermediate products) were treated for 35 minutes at 30° C. in a 10% aqueous solution of trimethylamine and for 5 minutes at room temperature in a 5% sulfuric acid solution and then rinsed for 10 minutes with running water, to obtain membranes having quaternary ammonium ligands (hereinafter: Q membranes).

Example 8

Introduction of Sulfonic Acid Ligands (S Membrane)

Activatingly crosslinked membranes (intermediate products) were treated for 45 minutes at 80° C. in an aqueous solution of 30% sodium sulfite and 2.5% $Na_2HPO_4 \times H_2O$ at a pH of 8.0 and then rinsed for 10 minutes with running water, for 5 minutes with 35 g of a 1% HCl solution, for 2×5 minutes with 30 g each time of an aqueous 1 M NaCl solution, for 5 minutes with 500 g of a 5% $H_2SO_4$ solution, and for 10 minutes with running water, to obtain membranes having sulfonic acid ligands (S membranes).

Example 9

Introduction of Phenyl Ligands (Ph Membrane)

Activatingly crosslinked membranes (intermediate products) were treated for three hours at room temperature with an aqueous solution of 1% aniline in a 0.1 M potassium phosphate (KPi) buffer at a pH of 7.8, and the moist samples were left for 19 hours in a sealed vessel. 15 minutes of rinsing with running water were followed by rinsing for 15 minutes with a 1 M aqueous NaCl solution and for 15 minutes with running water, to obtain membranes having phenyl ligands (Ph membranes).

Example 10

Introduction of Butyl Ligands (Butyl Membrane)

Activatingly crosslinked membranes (intermediate products) were treated for three hours at room temperature with an aqueous solution of 1% butylamine in a 0.1 M KPi buffer at a pH of 11.4, and the moist samples were left for 19 hours in a sealed vessel. 15 minutes of rinsing with running water were followed by rinsing for 15 minutes with a 1 M aqueous NaCl solution and for 15 minutes with running water, to obtain membranes having butyl ligands (butyl membranes).

Example 11

Introduction of Hexyl Ligands (Hexyl Membrane)

Activatingly crosslinked membranes (intermediate products) were treated for three hours at room temperature with an aqueous solution of 1% hexylamine in a 0.1 M KPi buffer at a pH of 11.3, and the moist samples were left for 19 hours in a sealed vessel. 15 minutes of rinsing with running water were followed by rinsing for 15 minutes with a 1 M aqueous NaCl solution and for 15 minutes with running water, to obtain membranes having hexyl ligands (hexyl membranes).

Example 12

Introduction of Octyl Ligands (Octyl Membrane)

Activatingly crosslinked membranes (intermediate products) were treated for 3 hours at room temperature with a solution of 1% octylamine and 35% diglyme in a 0.1 M KPi buffer at a pH of 10.9, and the moist samples were left for 19 hours in a sealed vessel. 15 minutes of rinsing with running water were followed by rinsing for 15 minutes with a 1 M aqueous NaCl solution and for 15 minutes with running water, to obtain membranes having octyl ligands (octyl membranes).

Example 13

Drying of the Adsorption Membrane According to the Invention

CA membranes were hydrolyzed in a 0.5 M aqueous sodium hydroxide solution for 30 minutes at room temperature, subsequently, without rinsing, crosslinked with a solution of 30% 1,4-butanediol diglycidyl ether and 0.1% sodium borohydride in a 0.5 M aqueous sodium hydroxide solution at room temperature for 2.5 hours, then derivatized with trimethylamine, and tested with regard to their static binding capacity both in an undried state and in a dried state, having been dried at 80° C. in a circulating air drying cabinet. The results are reported in table 5.

Example 14

Determination of the Fraction of Ultrapores of the Entire Pore Volume of the Membranes To determine the fraction of ultrapores of the entire pore volume of the membranes, the CA membrane was hydrolyzed analogously to example 2 at different sodium hydroxide solution concentrations, rinsed with 0.5 M NaOH, crosslinked as in example 2, and modified with sulfonic acid ligands as in example 8 (membranes 1-6). For comparison, the membrane from example 1 (membrane A) and the microfiltration membranes, known in the prior art, from Sartorius Stedim Biotech GmbH having pore sizes in the range 0.2-0.45 µm (membranes B-F) were used.

The Blue Dextran used was commercially available dextran from Leuconostoc mesenteroides, strain B 512, modified with Reactive Blue 2 dye, about 0.1 mmol of Reactive Blue 2 per gram of dextran (Blue Dextran Molecular Weight (Mw) 2 000 000 from Sigma, St. Louis, Mo., USA, product number D 5751, CAS number: 87915-38-6).

The hydrodynamic diameter d of this Blue Dextran can be calculated with the help of the Mark-Houwink-Sakurada equation:

$$d\ [nm] = 0.054 \times Mw^{0.5}$$

and is 76.4 nm.

Ultrapores are, as defined above, pores which are not accessible to Blue Dextran.

The pore volume accessible to water is referred to as Vw $[cm^3]$. It is assumed that all membrane pores are accessible to water, and therefore Vw corresponds to the entire pore volume of the membrane.

The pore volume accessible to Blue Dextran is referred to as Vd $[cm^3]$.

The pore volume of the ultrapores which is not accessible to Blue Dextran is referred to as Vp $[cm^3]$.

Vp is increased by the method according to the invention, in which the cellulose ester membrane swells during the hydrolysis.

The following equations apply: Vw=Vd+Vp and Vp=Vw−Vd

The percentage of pores inaccessible to Blue Dextran in the membrane is % Vp=100×(Vw−Vd)/Vw.

The pore volume Vd accessible to Blue Dextran is determined by the following method:

10 ml of a solution of Blue Dextran in RO water of a known concentration (c0) are filtered through a wet membrane. As a result, the water from the pore volume accessible to Blue Dextran is replaced with the Blue Dextran solution. The prerequisite for the technique is that the membrane does not adsorptively bind the Blue Dextran. This is the case for unmodified cellulose hydrate membranes, crosslinked and uncrosslinked. A membrane having a diameter of 50 mm (i.e., an area of 19.6 $cm^2$) is intensively washed for 15 minutes with running RO water. The wet membrane is then incorporated into a filtration housing, and 10 ml of Blue Dextran solution having a concentration of 5 mg/ml (c0) are filtered through the membrane at a pressure of 0.1 bar. The membrane is then removed from the filtration housing, a section having a diameter of 47 mm (i.e., an area of 17.3 $cm^2$) is punched out of the middle (in order to remove the sealed edges of the membrane) and dabbed dry with a laboratory towel (Kimtech Science, 200, 2, 21×20 cm, white, 7101).

Afterwards, the membrane is shaken in an exactly determined amount (volume V=5.0 ml) of RO water in a sealed vessel for 20 hours at 80 rpm. The concentration of the Blue Dextran solution (c) is then determined photometrically at 618 nm. The extinction coefficient E (1 mg/ml; 1 cm) of the Blue Dextran solution is 0.896. From the concentration of the Blue Dextran solution, the pore volume accessible to Blue Dextran is calculated:

$$Vd\ [cm^3] = c \times V/c0$$

The pore volume accessible to water is determined by the following method:

The membrane sample is intensively washed for 15 minutes with running RO water. The water adhering to the membrane is dabbed off with the laboratory towel, and the wet membrane is weighed. Afterwards, the membrane is dried at 80° C. in a circulating air drying cabinet for 30 minutes, and the dried membrane is weighed. The weight difference between the wet membrane and dry membrane corresponds to the amount of water in the membrane (Vw). A water density of 1.0 $g/cm^3$ is assumed.

From % $Vp = 100 \times (Vw - Vd)/Vw$ the percentage of the pore volume not accessible to Blue Dextran in the entire pore volume is calculated.

With increasing sodium hydroxide solution concentration in the hydrolysis of the cellulose acetate membrane, the swelling becomes stronger, the degree of swelling increases, the permeability of the membrane decreases, the membrane thickness increases, the fraction of ultrapores of the entire pore volume increases, and the binding capacity increases, as is apparent from table 1 below.

TABLE 1

| | Hydrolysis c (NaOH) [M] | Rinsing after hydrolysis c (NaOH) [M] | Vp [%] | Permeability, 10 mM KPi, pH 7 S membrane [ml/(min × bar × cm²)] | Binding capacity, lysozyme S membrane [mg/cm²] | Degree of swelling [—] |
|---|---|---|---|---|---|---|
| 1 | 0.20 | 0.5 | 16% | 515 | 0.75 | 1.4 |
| 2 | 0.40 | 0.5 | 25% | 341 | 1.40 | 2.1 |
| 3 | 0.50 | 0.5 | 30% | 180 | 1.71 | 4.1 |
| 4 | 0.60 | 0.5 | 34% | 73 | 1.99 | 10.0 |
| 5 | 0.75 | 0.5 | 39% | 8 | 2.23 | 90.1 |
| 6 | 1.00 | 0.5 | 45% | 4 | 2.40 | 208.6 |

Example 15

Protein Separation

Five layers of membranes from examples 9, 10, 11, and 12 were, in each case, arranged over one another, and the membrane stack was clamped into a membrane holder. Each membrane stack had a respective active membrane area of 100 cm², an inflow area of 20 cm², and a bed height (thickness of the membrane stack) of 1.4 mm in the membrane holder, and was flooded with RO water in order to displace the air from the membranes and subsequently connected to a Fast Protein Liquid Chromatography (FPLC) system (Äkta Prime from General Electric Health Care). Afterwards, the membranes, i.e., the membrane stack, were tested with regard to protein separation with a test program comprising four steps. In the test program, use is made of buffer A (a 1.7 M $(NH_4)_2SO_4$ solution in a 50 mM KPi buffer having a pH of 7.0) and buffer B (a 50 mM KPi buffer having a pH of 7.0). The four steps of the test program are specified below:

1. Equilibrating the membranes with 20 ml of buffer A, which flows through the membranes at a flow rate of 10 ml/min,
2. Loading the membranes with 2 ml of a solution, prefiltered by means of a 0.45 μm filter, of 0.5 mg/ml cytochrome C, 0.5 mg/ml a-chymotrypsinogen, 0.5 mg/ml lysozyme, and 0.5 mg/ml myoglobin in buffer A, which is applied via a loop at a flow rate of 10 ml/min,
3. Washing the loaded membrane with 18 ml of buffer A at a flow rate of 10 ml/min, and
4. Eluting the loaded and washed membranes with 150 ml of buffer B in buffer A at a linear gradient of 40-100% and at a flow rate of 10 ml/min.

The eluate was tested with regard to the amount of the eluted proteins and their separation by measurement of the optical density (OD) at 280 nm. The result is shown in table 2 and displayed graphically in FIGS. 6, 7, 8, and 9.

Evaluation of the Membranes

The membranes obtained were evaluated in the manner described below:

1) Flow Rate Determination

Membranes having an active membrane area of 12.5 cm² were each incorporated into a housing, and the time taken for the filtration of 100 ml of water or buffer was measured. The flow rate figures reproduced in table 5 for membranes reacted with functional groups relate to the corresponding binding buffer. The same buffers were used as for the determination of the binding capacities described below.

2) Determining the Static Binding Capacity of Q Membranes

Membrane samples having, in each case, an active membrane area of 17.6 cm² were shaken in 35 ml of 20 mM Tris/HCl, pH 7.3, for 3×5 minutes at about 80 revolutions per minute (rpm). Afterwards, the membrane samples were shaken in 35 ml of a solution of 2 mg/ml bovine serum albumin (BSA) solution in 20 mM Tris/HCl, pH 7.3 for 12-18 hours at 20-25° C. at about 80 rpm. Subsequently, the membrane samples were rinsed for 2×15 minutes in, in each case, 35 ml of 20 mM Tris/HCl, pH 7.3. Afterwards, the membrane samples were shaken in 20 ml of 20 mM Tris/HCl, pH 7.3+1 M aqueous NaCl solution. The amount of the eluted protein was determined by measurement of the optical density (OD) at 280 nm.

3) Determining the Static Binding Capacity of S Membranes

Membrane samples having, in each case, an active membrane area of 17.6 cm² were shaken in 35 ml of 10 mM KPi, pH 7.0, for 3×5 minutes at about 80 rpm. Afterwards, the membrane samples were shaken in 35 ml of a solution of 2 mg/ml lysozyme in 10 mM KPi, pH 7.6 for 12-18 hours at 20-25° C. at about 80 rpm. Subsequently, the membrane samples were rinsed for 2×15 minutes in, in each case, 35 ml of 10 mM KPi, pH 7.0. Afterwards, the membrane samples were shaken in 20 ml of 10 mM KPi, pH 7.0+1 M aqueous

TABLE 2

Protein separation according to example 15

| Membrane | Peak position | Peak 1 | Peak 2 | Peak 3 | Peak 4 |
|---|---|---|---|---|---|
| Example 9 | Retention volume [ml] | 5.6 | 29.4 | 41.0 | 64.5 |
| Phenyl membrane | Conductivity [mS/cm] | 177 | 160 | 121 | 105 |
| | Buffer B [%] | 0 | 43.8 | 48.3 | 57.8 |
| Example 10 | Retention volume [ml] | 6.2 | 31.5 | — | — |
| Butyl membrane | Conductivity [mS/cm] | 177 | 141 | — | — |
| | Buffer B [%] | 0 | 44.6 | — | — |
| Example 11 | Retention volume [ml] | 5.7 | 34.0 | — | — |
| Hexyl membrane | Conductivity [mS/cm] | 176 | 131 | — | — |
| | Buffer B [%] | 0 | 45.6 | — | — |
| Example 12 | Retention volume [ml] | 5.5 | 35.6 | 68.3 | — |
| Octyl membrane | Conductivity [mS/cm] | 178 | 128 | 102 | — |
| | Buffer B [%] | 0 | 46.3 | 59.3 | — |

NaCl solution. The amount of the eluted protein was determined by measurement of the optical density (OD) at 280 nm.

4) Determining the Static Binding Capacity of Ph Membranes, Butyl Membranes, Hexyl Membranes, and Octyl Membranes Membrane samples having an active membrane area of 3.1 cm$^2$ were clamped into a polycarbonate attachment and connected to a peristaltic pump. Solutions were pumped in the following order through the membranes with the help of the peristaltic pump at a flow rate of 2 ml/min:

1. 10 ml of 0.05 M KPi+1 M $(NH_4)_2SO_4$, pH 7.0
2. 20 ml of 1 mg/ml gamma-globulin in 0.05 M KPi+1 M $(NH_4)_2SO_4$, pH 7.0
3. 20 ml of 0.05 M KPi+1 M $(NH_4)_2SO_4$, pH 7.0
4. 10 ml of 0.05 M KPi, pH 7.0

The amount of the eluted protein in step 4 was determined by measurement of the optical density (OD) at 280 nm.

5) Determining the Running Time

The membrane samples from examples 2, 9, 10, 11, and 12 were dried for 20 minutes at 80° C. in a circulating air drying cabinet. After a five-minute cooling to room temperature, 10 µl of a 5.8% aqueous NaCl solution were applied in each case to the respective membrane, and the time taken for complete absorption of the solution into the membrane was measured with a stopwatch. The running time is specified in seconds.

The result of the determination of the flow rate and the running time of the membranes from examples 2, 9, 10, 11, and 12 is shown in table 3 below.

TABLE 3

| Example | Ligand | Flow rate | Binding capacity | Running time |
| --- | --- | --- | --- | --- |
| 2 | None (base membrane) | 84 | 0.03 | 5 |
| 9 | Phenyl | 90 | 0.82 | 10 |
| 10 | Butyl | 88 | 0.25 | 7 |
| 11 | Hexyl | 84 | 0.67 | 36 |
| 12 | Octyl | 112 | 0.66 | 617 |

6) Determining the Binding Capacity as a Function of the Concentration of the Ammonium Sulfate in the Buffer The binding capacities of a phenyl membrane produced as in example 9 were determined as described in point 4) "Determining the static binding capacity of Ph membranes, butyl membranes, hexyl membranes, and octyl membranes" in the section "Evaluation of the membranes", but with the difference that the concentration of ammonium sulfate was varied from 0 M to 1.0 M and the membranes were regenerated after each cycle of steps 1 to 4 in an additional step 5 with 10 ml of a 50% solution of ethylene glycol in RO water. The measured values obtained are shown in table 4 and displayed graphically in FIG. 10.

TABLE 4

| Ammonium sulfate [M] | Binding capacity, base membrane Example 2 | Binding capacity, phenyl membrane Example 9 |
| --- | --- | --- |
| 0 | 0.008 | 0.002 |
| 0.2 | 0.025 | 0.025 |
| 0.4 | 0.020 | 0.081 |
| 0.6 | 0.031 | 0.210 |
| 0.8 | 0.052 | 0.456 |
| 1.0 | 0.078 | 0.686 |

7) Confocal Laser Scanning Microscopy

Labeling the Membranes

An adsorption membrane from example 1 and an adsorption membrane according to the invention as per example 2 were provided with sulfonic acid ligands according to example 8. Together with an adsorption membrane from Sartorius Stedim Biotech GmbH, commercially available under the trade name Sartobind® S, having a sulfonic-acid-overlaid auxiliary polymer, the membranes were labeled with the OH-reactive fluorescent dye "5-DTAF" (5-(4,6-dichlorotriazinyl) aminofluorescein, excitation wavelength and emission wavelength of 492 nm and 516 nm, respectively Invitrogen). The incubation of the solution of the dye and also all following wash steps were carried out with, in each case, three membrane samples (diameter: 13 mm) in a filter holder with continuous rinsing at a flow rate of about 1 ml/min. Use was made, in each case, of 20 ml of a 5-DTAF solution in a 100 mM sodium hydrogen carbonate solution having a pH of 9.3 and having concentrations matched to the membrane, viz. 13.5 µg/ml 5-DTAF+100 mM NaCl solution for the membranes according to examples 1 and 2, and 25 µg/ml 5-DTAF+ 200 mM NaCl solution for the Sartobind® S membrane. Since it was suspected that the three-dimensional cation exchanger layer causes particularly effective shielding of the cellulose matrix, both the dye concentration and the salt concentration were increased for the Sartobind® S membrane. After rinsing for about 18 hours, the samples were subsequently washed in succession with, in each case, 100 ml of a 20% ethanol solution, a 1 M NaCl solution, and a 200 mM sodium phosphate buffer, pH 7.0. For the CLSM analysis, the second sample in the filter holder was used in each case because it had the best homogeneity of labeling.

Labeling and Clean Up of the Protein

Lysozyme (available from Sigma, St. Louis, Mo., USA; protein about 95%, about 50 000 units/mg of protein) was labeled with the $NH_2$-reactive fluorescent dye "Cy5 mono-Reactive NHS Ester" (available from GE Health Care Bio-Sciences AB, Uppsala, Sweden) in a sodium carbonate buffer, pH 9.3, and also subsequently cleaned up, firstly by gel filtration and then by HP ion exchange chromatography. By appropriate selection of the chromatographic fractions, the singly labeled lysozyme was obtained in a pure form. Afterwards, concentration was effected by means of ultrafiltration, to the concentration necessary for the binding experiment. The concentration of the labeled lysozyme was determined by means of a UV-Vis photometer (measurement of the absorbances at 280 nm and 650 nm).

Incubating the Membranes with Protein

Samples of the membranes labeled with 5-DTAF were punched out with a diameter of 5 mm and incubated for four hours in a solution of the labeled lysozyme having a concentration of 0.6 g/L in a 200 mM sodium phosphate buffer, pH 7.0+50 mM aqueous NaCl solution (for 1 cm$^2$ samples, 4.1 ml of protein solution were used in each case). Afterwards, the samples were washed with the buffer for 15 minutes.

CLSM Analysis

The analysis was effected with the CLSM system Leica TCS SP. Each sample was examined in a 200 mM sodium phosphate buffer from both surfaces. First, a suitable signal amplification was determined (criteria: suppressed autofluorescence of the membrane; the maximum of the signal amplification was set with the help of the histogram in the evaluation software "Zeiss LSM Image Browser" in order to avoid local overexposure) and z=0 was identified (criteria: high scattering intensity and subsequent first identification of the pore morphology with further reduction of the distance to the sample). Afterwards, the characteristic morphology of the Sartobind® S membranes known from SEM was searched for in x,y-scans at different z-positions. Afterwards, detailed x,y-scans of the two excitation wavelengths (488 nm for 5-DTAF, 633 nm for Cy5) were carried out in a narrow range of different z-positions (at a depth of about 20 micrometers, at intervals of 1 micrometer in both directions). For each sample and each orientation, these scans were carried out, in each case, for three different positions. The Sartobind® S sample was analyzed first; the settings chosen for this sample (z-position and signal amplification) were retained for the analysis of the other membrane samples. Because the signal intensities of the membrane according to the invention as per example 2 were very much higher at 633 nm than for the other two membranes, a reduction of the signal amplification was made: "Gains" (488 nm/633 nm)
Sartobind® S membrane: 426/643
Membrane according to example 1: 426/669
Membrane according to example 2: 357/650

CLSM Evaluation

The evaluations were carried out with the help of the Zeiss LSM Image Browser 3.5.0.376. From the images obtained, detailed x,y-scans in a range of the z-positions of a depth of about 20 μm for the upper side were selected. The images obtained were each displayed as 8-bit images having a resolution of 512×512 pixels, corresponding to 146.2×146.2 μm². FIGS. 2 to 4 show the overlapping of the two images of the distribution of lysozyme and of the pore morphology of the cellulose. Additionally, an intensity profile of the intensities for both fluorescent labels is also shown for each measurement at the upper right edge of the picture.

Results of the Experiments

The results of the experiments are shown in table 5 below.

TABLE 5

| Membrane from example | Remark | Ligand | Protein | Flow rate | Binding capacity |
|---|---|---|---|---|---|
| 1 | | Q | BSA | 643 | 0.07 |
| | | S | Lysozyme | 664 | 0.01 |
| | | Ph | Gamma-globulin | 570 | 0.2 |
| 2 | | Q | BSA | 44 | 0.92 |
| | | S | Lysozyme | 38 | 2.06 |
| | | Ph | Gamma-globulin | 31 | 1.26 |
| 3 | | Q | BSA | 20 | 1.13 |
| | | S | Lysozyme | 24 | 2.85 |
| 4 | | Q | BSA | 158 | 0.74 |
| | | S | Lysozyme | 167 | 3.11 |
| | | S | Gamma-globulin | 167 | 0.44 |
| 5 | LiOH | Q | BSA | 70 | 1.18 |
| | NaOH | Q | BSA | 109 | 0.93 |
| | KOH | Q | BSA | 519 | 0.08 |
| 13 | Undried | Q | BSA | 213 | 0.94 |
| | Dried | Q | BSA | 239 | 0.92 |

Comparative Example 1

Simultaneous hydrolysis and crosslinking as in example 1, sample K10C of WO 2007/017085 A2, but with 1,4-butanediol diglycidyl ether instead of epichlorohydrin, under non-swelling conditions.

A CA membrane as defined above and a 0.65 μm cellulose acetate membrane as in example 1, sample K10C of WO 2007/017085 A2 having a water flow rate of 65 ml/(min×bar×cm²) were used as starting membranes.

The cellulose acetate membranes were heated to 47° C. in 100 g of water, 10 g of $Na_2SO_4$, and 1 g of 1,4-butanediol diglycidyl ether, and 10 g of a 1 M aqueous sodium hydroxide solution were metered in over 30 minutes. The membranes were further treated in the solution for 3.5 hours at 47° C. and subsequently rinsed for 30 minutes with running water. Quaternary ammonium ligands were introduced into the membranes to obtain Q membranes. The hydrolyzed and crosslinked Q membrane obtained from the CA membrane exhibited a water flow rate of 589 ml/(min×bar×cm²), a degree of swelling of 1.2, and a binding capacity for BSA of 0.04 mg/cm². The hydrolyzed and crosslinked Q membrane obtained from the cellulose acetate membrane according to example 1, sample K10C of WO 2007/017085 A2 exhibited a water flow rate of 66 ml/(min×bar×cm²), a degree of swelling of 1.0, and a binding capacity for BSA of 0.04 mg/cm².

Comparative Example 2

Attempt to Swell Previously Hydrolyzed Cellulose Hydrate Membranes

A CA membrane as defined above and used as a starting membrane was hydrolyzed for three minutes at room temperature with a 15% potassium hydroxide solution in 80% ethanol and subsequently rinsed for three minutes with a 6.8% acetic acid solution, twice with ethanol, and for 15 minutes with running RO water. The hydrolyzed membrane obtained was treated for 30 minutes at room temperature with a 0.6 M aqueous sodium hydroxide solution and then rinsed three times for 10 minutes with a 0.5 M aqueous sodium hydroxide solution. Subsequently, the membrane was treated for 30 minutes at room temperature with a 30% solution of 1,4-butanediol diglycidyl ether in a 0.1 M aqueous sodium hydroxide solution and 0.1% aqueous sodium borohydride solution, whereupon the moist membrane was left to stand for 20 hours in a closed vessel at room temperature. Finally, the membrane obtained was rinsed for 30 minutes with running water.

The water flow rate of the hydrolyzed and crosslinked cellulose hydrate membrane thus produced was 688 ml/(min×bar×cm²), and the degree of swelling was 1.06.

Quaternary ammonium ligands or sulfonic acid ligands were, as described in example 7 or 8, introduced into two samples of the membrane to obtain a Q membrane and an S membrane. The Q membrane exhibited a binding capacity for BSA of 0.044 mg/cm², and the S membrane exhibited a binding capacity for lysozyme of 0.067 mg/cm².

What is claimed is:

1. A crosslinked cellulose hydrate membrane having a porous double structure consisting of
    micropores having a diameter in the range from >100 nm to 20 μm, and
    ultrapores which have a diameter in the range from <100 nm and which are not accessible to Blue Dextran having an average molecular weight Mw of 2 000 000,
    wherein the fraction of the volume of the ultrapores is more than 15% of the entire pore volume accessible to water,
    wherein hydrophobic ligands, selected from $C_1$-$C_{20}$-alkyl and their derivatives or $C_6$-$C_{25}$-aryl and their derivatives or $C_7$-$C_{25}$-arylalkyl and their derivatives or —[$(CH_2)_m$-O—]n-R, where m is 2 or 3, n is a whole number greater than or equal to 1, and R is —H or —$C_1$-$C_5$-alkyl, are bonded to the membrane, and
    the crosslinked cellulose hydrate membrane is produced by a method comprising:
    providing a cellulose ester membrane having a pore diameter in the range from 0.1 to 20 μm,
    optionally pretreating the cellulose ester membrane in a medium at a temperature in the range from about 20° C. to about 100° C., hydrolyzing the optionally pretreated cellulose ester membrane under a swelling condition, wherein the hydrolysis is carried out in a hydrolysis medium consisting of water and one or both of sodium hydroxide and lithium hydroxide, wherein the concentration of one or both of sodium hydroxide and lithium hydroxide in the hydrolysis medium is in the range of 0.4 to 10% by weight, based on the hydrolysis medium, crosslinking the hydrolyzed membrane with at least one crosslinking agent, wherein said crosslinking is carried out after hydrolyzing in sequence, and introducing the hydrophobic ligands into the membrane.

2. The cellulose hydrate membrane as claimed in claim 1, wherein the micropores which stretch from a first main surface of the membrane through the membrane to a second main surface are connected with formation of channels communicating with one another, and the ultrapores stretch from an inner surface of the micropores into a material forming the structure of the membrane, forming a dead end, and/or connect neighboring micropores with one another.

3. A method for producing a crosslinked cellulose hydrate membrane having a porous double structure as claimed in claim 1, wherein:

the hydrolysis is carried out in a period in the range from about 0.1 to about 60 minutes, and the at least one crosslinking agent has at least 2 functional groups in the molecule which are reactive with the hydroxyl groups of the cellulose.

4. The method as claimed in claim 3, wherein the alkali metal hydroxide is sodium hydroxide.

5. The method as claimed in claim 3, wherein a temperature of the hydrolysis medium during the hydrolysis is in the range from 10° C. up to a boiling point of the hydrolysis medium.

6. The method as claimed in claim 3, wherein the crosslinking agent is selected from the group consisting of diepoxide compounds, diisocyanates, epichlorohydrin, epibromohydrin, dimethyl urea, dimethylethyleneurea, dimethylchlorosilane, bis(2-hydroxyethyl) sulfone, divinyl sulfone, alkylene dihalogen, hydroxyalkylene dihalogen, and glycidyl ethers.

7. The method as claimed in claim 6, wherein the crosslinking agent is a diepoxide compound.

8. The method as claimed in claim 3, wherein the crosslinking is carried out in an aqueous medium, an organic solvent, or a mixture of water and an organic solvent.

9. The method as claimed in claim 3, wherein the crosslinking is carried out in the presence of a crosslinking catalyst.

10. The method as claimed in claim 8, wherein the crosslinking is carried out at a temperature in the range from about 4° C. up to a boiling point of the crosslinking medium.

11. The method as claimed in claim 3, wherein the crosslinking is carried out in a period in the range from about 10 minutes to about 100 hours.

12. The method as claimed in claim 3, wherein the hydrophobic ligands are introduced during the crosslinking or after the crosslinking.

13. The method as claimed in claim 12, wherein the membrane is dried after introducing the hydrophobic ligands.

14. The method as claimed in claim 13, wherein the membrane is dried from a medium which comprises a pore-stabilizing compound.

15. An apparatus for hydrophobic interaction chromatography, comprising at least one crosslinked cellulose hydrate membrane as claimed in claim 1.

16. An apparatus for removing one or more contaminants comprising at least one crosslinked cellulose hydrate membrane as claimed in claim 1.

17. A method for removing one or more contaminants from a sample comprising:

applying the sample comprising said one or more contaminants to the apparatus of claim 16, wherein said at least one crosslinked cellulose hydrate membrane is configured to bind to said one or more contaminants, thereby separating said one or more contaminants from the sample.

18. An apparatus for selective adsorption and subsequent desorption of one or more target substances comprising at least one crosslinked cellulose hydrate membrane as claimed in claim 1.

19. A method for selective adsorption and subsequent desorption of one or more target substances comprising:

applying a sample comprising said one or more target substances to the apparatus of claim 18, wherein said at least one crosslinked cellulose hydrate membrane is configured to bind to said one or more target substances;

washing said at least one crosslinked cellulose hydrate membrane that is applied with the sample; and eluting the one or more target substances from the washed membrane.

* * * * *